US006297059B1

(12) United States Patent
Song et al.

(10) Patent No.: US 6,297,059 B1
(45) Date of Patent: Oct. 2, 2001

(54) TRIGGERED OPTICAL BIOSENSOR

(75) Inventors: Xuedong Song; Basil I. Swanson, both of Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/338,457

(22) Filed: Jun. 22, 1999

Related U.S. Application Data
(60) Provisional application No. 60/090,265, filed on Jun. 22, 1998.

(51) Int. Cl.[7] .................................................. G01N 33/566
(52) U.S. Cl. .......................... 436/501; 436/518; 436/514; 436/2; 436/172; 435/4; 435/7.1; 435/287.1; 435/287.2; 435/288.7
(58) Field of Search ..................................... 436/501, 518, 436/514, 2, 172; 435/4, 7.1, 287.1, 287.2, 288.7

(56) References Cited

U.S. PATENT DOCUMENTS

| 5,194,393 | 3/1993 | Hugl et al. ............................ 436/525 |
| 5,322,794 | 6/1994 | Davenport ............................. 436/71 |
| 5,711,915 | 1/1998 | Siegmund et al. .................... 422/681 |
| 5,741,712 | 4/1998 | Cornell et al. ....................... 436/501 |
| 5,756,355 | 5/1998 | Lang et al. .......................... 435/7.21 |
| 5,846,814 | * 12/1998 | Galla et al. . |
| 5,922,594 | 7/1999 | Lofas .................................. 435/291 |

FOREIGN PATENT DOCUMENTS

WO 98/00714 * 1/1998 (WO) .

OTHER PUBLICATIONS

B. A. Cornell et al., "A Biosensor That Uses Ion–Channel Switches," Nature, vol. 387, pp. 580–583 (Jun. 5, 1997).
M. J. Hope et al., "Production of Large Unilamellar Vesicles by a Rapid Extrusion Procedure: Characterization of Size Distribution, Trapped Volume and Ability to Maintain a Membrane–Potential," Biochim. Biophys. Acta, vol. 812, pp. 55–65 (1985).
P. L. Felgner et al., "Asymmetric Incorporation of Trisialoganglioside into Dipalmitoylphosphatidylcholine Vesicles," Biochemistry, vol. 20, pp. 2168–2172 (1981).
Xuedong Song et al., "Optical Biosensor Based on Fluorescence Resonance Energy Transfer: Ultrasensitive and Specific Detection of Protein Toxins," J. Am. Chem. Soc. 120, pp. 11514–11515 (Oct. 27, 1998).
Xuedong Song et al., "Direct, Ultrasensitive, and Selective Optical Detection of Protein Toxins Using Multivalent Interactions," Anal. Chem. vol. 71, No. 11, pp. 2097–2107 (Jun. 1, 1999).

(List continued on next page.)

Primary Examiner—Long V. Le
Assistant Examiner—Minh-Quan K. Pham
(74) Attorney, Agent, or Firm—Bruce H. Cottrell

(57) ABSTRACT

An optical biosensor is provided for the detection of a multivalent target biomolecule, the biosensor including a substrate having a bilayer membrane thereon, a recognition molecule situated at the surface, the recognition molecule capable of binding with the multivalent target biomolecule, the recognition molecule further characterized as including a fluorescence label thereon and as being movable at the surface and a device for measuring a fluorescence change in response to binding between the recognition molecule and the multivalent target biomolecule.

11 Claims, 21 Drawing Sheets

OTHER PUBLICATIONS

Chii–Shiarng Chen et al., "Changes in the Spectral Properties of a Plasma Membrane Lipid Analog During the First Seconds of Endocytosis in Living Cells," Biophysical Journal, vol. 72, pp. 37–50 (Jan. 1997).

Richard E. Pagano et al., "A Novel Fluorescent Ceramide Analogue for Studying Membrane Traffic in Animal Cells: Accumulation at the Golgi Apparatus Results in Altered Spectral Properties of the Sphingolipid Precursor," The J. of Cell Biology, vol. 113, No. 6 (Jun. 1991).

Eidels et al. (Dec. 1983). Membrane receptors for bacterial toxins. Microbiol. Rev. 47(4):596–620.*

Angstrom et al. (Dec. 1994). Delineation and comparison of ganglioside–binding epitopes for the toxins of *Vibrio cholerae, Escherichia coli, and Clostridium tetani*: Evidence for overlapping epitopes. PNAS USA. 91:11859–11863.*

Terrettaz et al. (1993). Protein binding to supported lipid membranes: investigation of the cholera toxin–ganglioside interaction by simultaneous impedance spectroscopy and surface plasmon resonance. Langmuir. 9:1361–1369.*

Sackmann (Jan. 5, 1996). Supported membranes: Scientific and practical applications. Science. 271:43–48.*

Kemeny (1997). Enzyme–linked immunoassay. In Immunochemistry 1, A Practical Approach. p. 147–145.*

Song et al. (May 1998). Optical signal transduction triggered by protein–ligand binding: Detection of toxins using multivalent binding. J. Am. Chem. Soc. 120:4873–4874.*

Keinanen et al. (1994). Biosynthetic lipid–tagging of antibodies. FEBS Letters. 346:123–126.*

Laukkanen et al. (1995). Use of genetically engineered lipid–tagged antibody to generate fuctional europium chelate–loaded liposomes application in fluoroimmunoassay. J Immunol. Methods. 185:95–102.*

* cited by examiner

R-lyso-GM1

$B_{FL}$-GM1 (Donor)

$B_{558/568}$-GM1 (Acceptor)

TRIGGERED OPTICAL BIOSENSOR

This application claims the benefit of U.S. Provisional application No. 60/090,265, filed Jun. 22, 1998.

The present invention relates to triggered optical biosensors, i.e., optical biosensors triggered by a recognition or binding event. This invention was made with government support under Contract No. W-7405-ENG-36 awarded by the U.S. Department of Energy. The government has certain rights in the invention.

FIELD OF THE INVENTION

BACKGROUND OF THE INVENTION

Biological sensors are based on the immobilization of a recognition molecule at the surface of a transducer (a device that transforms the binding event between the target molecule and the recognition molecule into a measurable signal). In one prior approach, the transducer has been sensitive to any binding, specific or non-specific, that occurred at the transducer surface. Thus, for surface plasmon resonance or any other transduction that depended on a change in the index of refraction, such sensors have been sensitive to both specific and non-specific binding. Another prior approach has relied on a sandwich assay where, for example, the binding of an antigen by an antibody has been followed by the secondary binding of a fluorescently tagged antibody that is also in the solution along with the protein to be sensed. In this approach, any binding of the fluorescently tagged antibody will give rise to a change in the signal and, therefore, sandwich assay approaches have also been sensitive to specific as well as non-specific binding events. Thus, selectivity of many prior sensors has been a problem.

Another previous approach where signal transduction and amplification have been directly coupled to the recognition event is the gated ion channel sensor as described by Cornell et al., "A Biosensor That Uses Ion-Channel Switches", Nature, vol. 387, Jun. 5, 1997. In that approach an electrical signal was generated for measurement. Besides electrical signals, optical biosensors have been described in U.S. Pat. No. 5,194,393 by Hugl et al. and U.S. Pat. No. 5,711,915 by Siegmund et al. In the later patent, fluorescent dyes were used in the detection of molecules.

Despite the recent progress in such signal transduction and amplification directly coupled to a recognition event, further improvements have been desired especially in the development of optical biosensors.

One object of the present invention is an optical biosensor using a transduction approach that amplifies specific binding events thereby amplifying both sensitivity and specificity.

Another object of the present invention is to provide an optical biosensor and process for use of optically tagged receptor molecules to trigger signal transduction and amplification by a recognition event.

Still another object of the present invention is to provide an optical biosensor and process for signal transduction based on aggregation of receptor molecules through either binding by a multivalent protein or binding of multiple receptor molecules to the same protein or protein clusters.

Yet another object of the present invention is an optical biosensor and process using optical signal transduction resulting from an internal reference by virtue of a simultaneous increase in a red fluorescence and a decrease in a blue fluorescence. This can be coupled with an isobestic point that can be used to reference the absolute intensity of fluorescence.

Another object of the present invention is the fabrication of biomimetic membranes (supported and hybrid phospholipid bilayers) containing the functionalized (optically tagged) receptor molecules such as glycolipid receptor molecules.

Another object of the present invention is to functionalize naturally occurring glycolipid receptors (e.g., Galβ1-3GalNAcβ1-4Gal(3-2αNeuAc)β1-4Glcβ1-1Cer, (GM1) with an optical tag such as fluorescent dye molecules.

Another object of the present invention is an optical biosensor and process using donor and acceptor dye molecules each of which is covalently attached to the recognition element to effect energy transfer upon aggregation following binding by a multivalent protein.

Another object of the present invention is an optical biosensor and process using hydrophobic optical tags (dye molecules) and hydrophobic linker molecules that can attach the optical tags to, e.g., a glycolipid so that the dye molecule stably resides in the upper leaf (layer) of a bilayer, e.g., a phospholipid bilayer. This can minimize non-specific interactions of the dye molecule with interferents.

Another object of the present invention is to provide an optical biosensor and process using optical transduction triggered by a specific protein binding event which results in energy transfer yielding both a decrease in the fluorescence of one dye species (e.g., blue emission) with a concomitant increase in the fluorescence of another dye species (e.g., red emission).

SUMMARY OF THE INVENTION

To achieve the foregoing and other objects, and in accordance with the purposes of the present invention, as embodied and broadly described herein, the present invention provides an optical biosensor for the detection of a multivalent target biomolecule including a substrate having a fluid membrane thereon, recognition molecules situated at a surface of said fluid membrane, the recognition molecule capable of binding with the multivalent target biomolecule, the recognition molecule further characterized as including a fluorescence label thereon and as being movable at the surface; and, a means for measuring a change in fluorescence properties in response to binding between the two different recognition molecules and the multivalent target biomolecule.

The present invention also provides an optical biosensor for the detection of a multivalent target biomolecule including a substrate having a fluid membrane thereon, at least two different recognition molecules situated at a surface of the fluid membrane, the recognition molecules capable of binding with the multivalent target biomolecule wherein at least one recognition molecule includes a fluorescence donor label thereon and at least one recognition molecule includes a fluorescence acceptor label thereon; and, a means for measuring a change in fluorescence properties in response to binding between the recognition molecules and the multivalent target biomolecule.

The present invention also provides an optical biosensor for the detection of a multivalent target biomolecule including a recognition element capable of binding with the multivalent target biomolecule wherein the recognition molecule includes a fluorescence label from the group of a fluorescence donor label and a fluorescence acceptor label thereon; a supporting surface for the recognition molecule situated thereon, wherein said supporting surface includes a fluorescence label from the group of a fluorescence donor label and a fluorescence acceptor label thereon, the supporting surface including a fluorescence donor label when the recognition molecule includes a fluorescence acceptor label and the supporting surface including a fluorescence acceptor label when the recognition molecule includes a fluorescence donor label and, a means for measuring a change in fluorescence properties in response to binding between the recognition molecules and the multivalent target biomolecule.

The present invention also provides a method of detecting a multivalent target biomolecule including contacting a sample with a sensor including a substrate having a fluid membrane thereon, at least two different recognition molecules situated at the surface of the fluid membrane, the recognition molecules capable of multivalent binding with the multivalent target biomolecule wherein at least one recognition molecule includes a fluorescence donor label thereon and at least one recognition element includes a fluorescence acceptor label thereon; and measuring a change in fluorescence properties in response to binding between the recognition molecule and the multivalent target biomolecule.

The present invention also provides an optical biosensor for the detection of a target biomolecule including a substrate having a fluid membrane thereon, recognition molecules situated at a surface of said fluid membrane, said recognition molecule bound with a selected multivalent biomolecule, said recognition molecules further characterized as including a fluorescence label, and, a means for measuring a change in fluorescent properties in response to competitive binding with said selected multivalent biomolecule by said recognition molecules and said target biomolecule.

DETAILED DESCRIPTION

The present invention is concerned with a triggered optical biosensor where signal transduction and amplification are directly coupled to optical signal transduction and amplification. One specific application of the present triggered optical biosensor can be the detection of protein toxins. Examples of protein toxins include botulinum, ricin, shiga and cholera. The present triggered optical biosensor may be used more generally for other detection applications such as detection of signature proteins for bio-agents or for envelope viruses, antibodies, viruses, other biomolecules and the like.

The present invention is further concerned with a triggered optical biosensor where a specific event triggers a change in fluorescence of chromophores attached to recognition molecules.

Figure 1A:
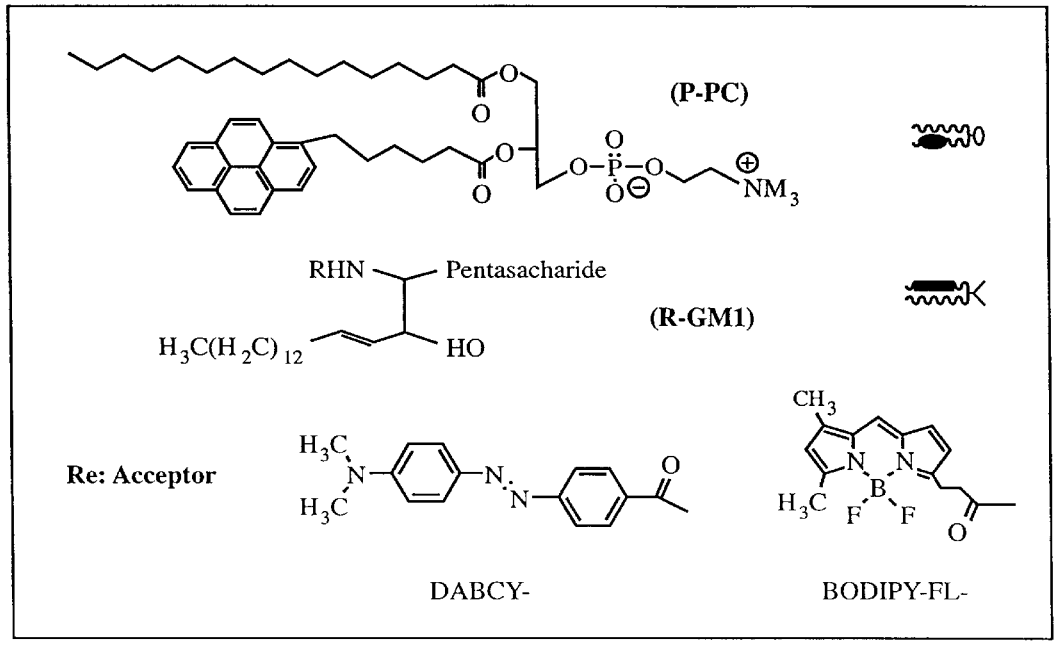
FIG. 1(a) shows chemical structures of materials used in the present invention and 1(b) shows a schematic representation of an optical biosensor based on fluorescence energy transfer in accordance with the present invention.
Figure 1B:
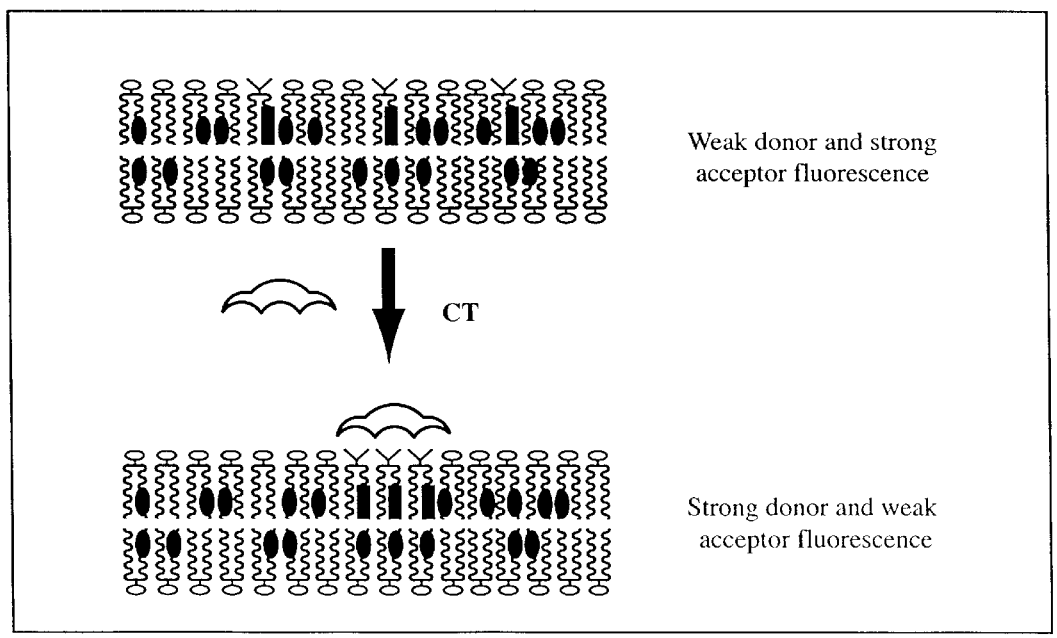
Figure 2:
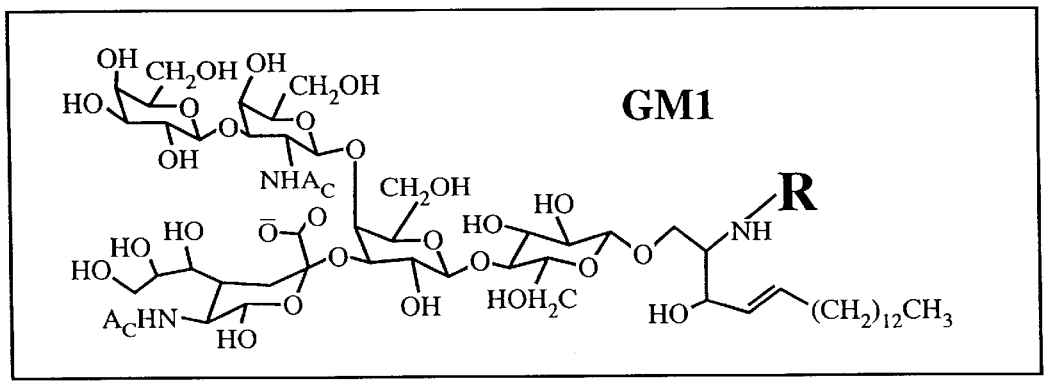
FIG. 2 shows chemical structures of labeling groups used to label ganlioside GM1 at the R site for use in the present invention.
Figure 2:
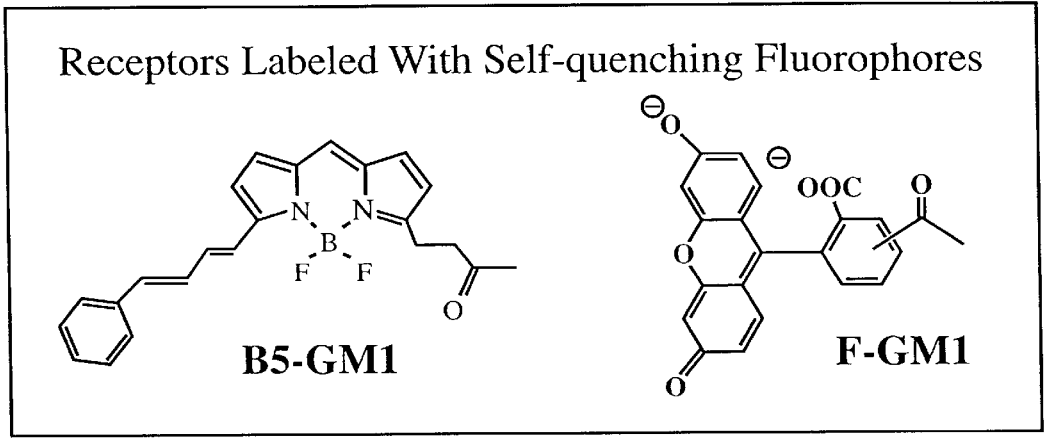
Figure 2:
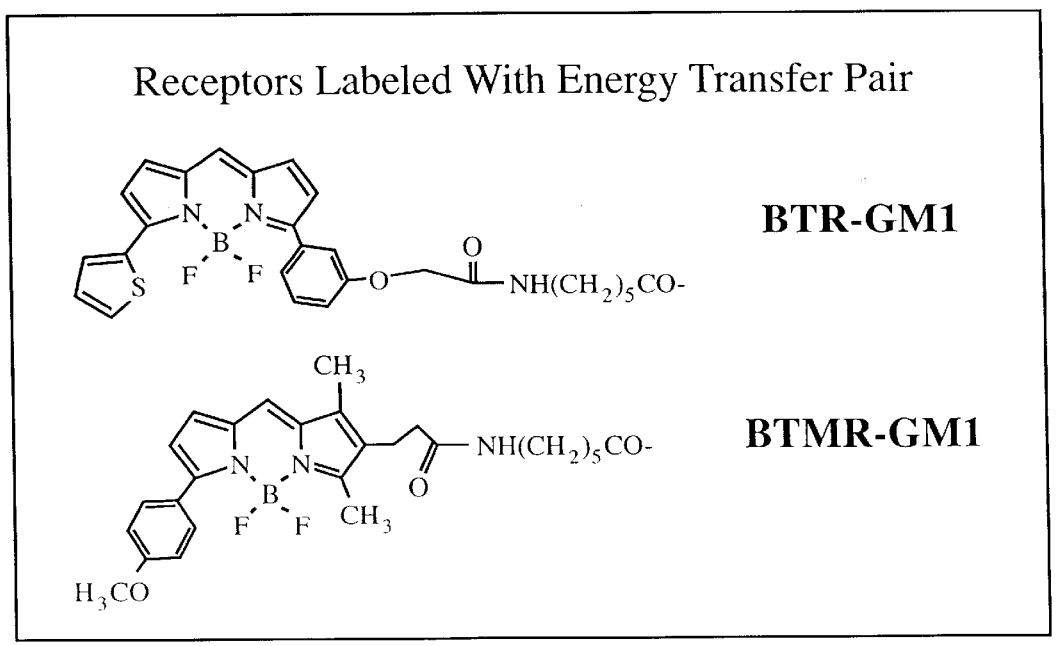
Figure 3:
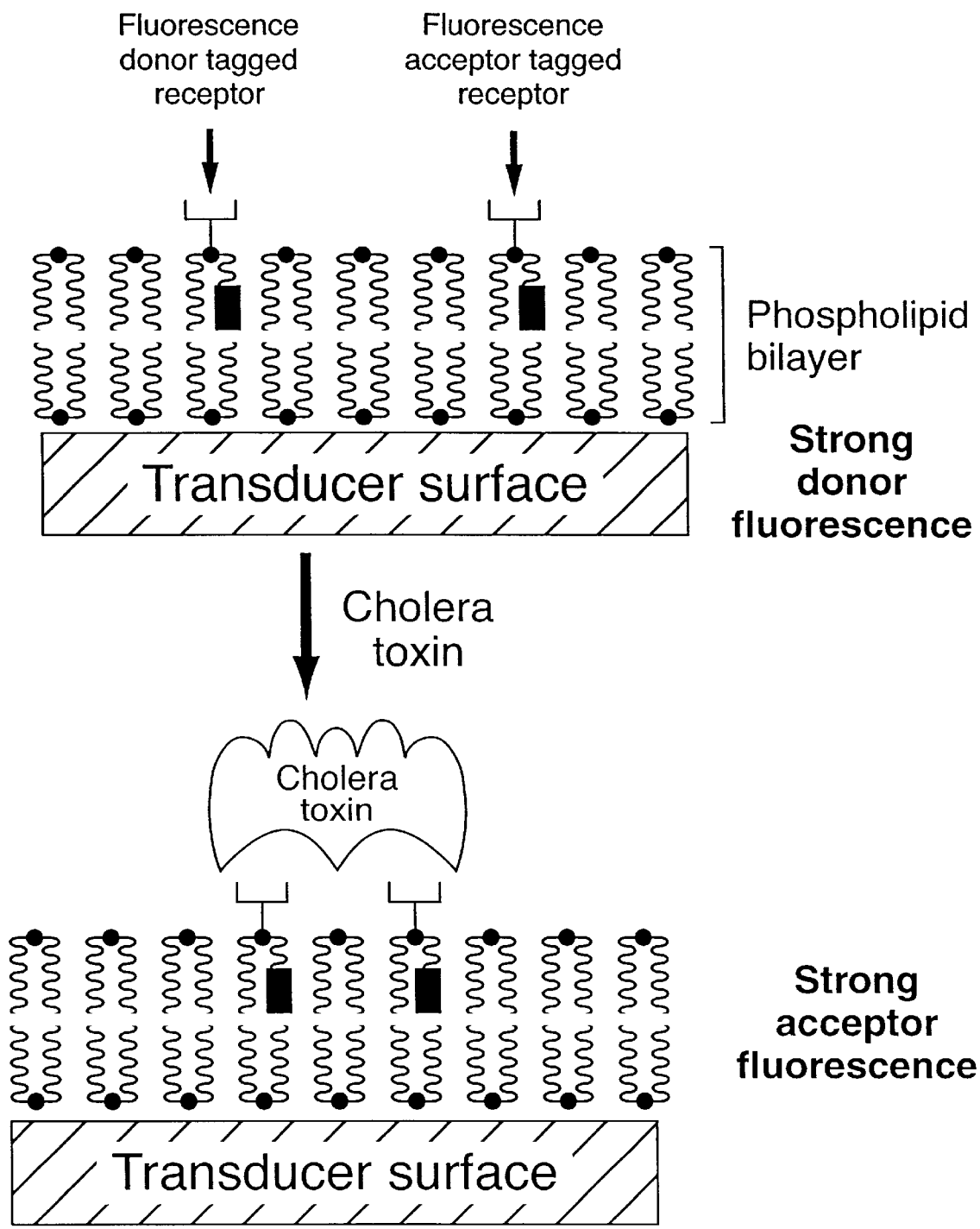
FIG. 3 shows a schematic representation of an optical biosensor based on fluorescence energy transfer in combination with a transducer in accordance with the present invention.

In FIG. 1(a) are shown chemical structures of various GM1 molecules and substituted GM1 molecules used in the present invention. A fluorescence acceptor is the result of substitution of 4-((4-dimethylamino)phenyl)azo)benzoic acid-, (DABCY-) or 4,4-difluoro-5,7-dimethyl-4-bora-3a,4a-diaza-s-indacene-3-propionic acid-, (BODIPY-FL-) in place of the R in R-GM1. Other labeling materials are shown in FIG. 2. FIG. 1(b) shows a schematic representation of a bilayer membrane with the materials illustrated in FIG. 1(a) both before the presence of a target biomolecule (in this case cholera toxin) and after the presence of the target biomolecule. In FIG. 3 is shown another schematic representation of an optical biosensor based on fluorescence energy transfer in combination with a transducer in accordance with the present invention.

In the present invention, the architecture of the fluid membranes can be as a regular bilayer membrane where both layers are deposited upon a support surface, can be a hybrid bilayer, e.g., where a first layer is covalently attached to an oxide surface, can be a selectively tethered bilayer on an oxide surface, where a membrane molecule is covalently bonded to the oxide substrate, or a bilayer cushioned by a polymer film. Supported membranes useful in the practice of the present invention are generally described by Sackmann, in "Supported Membranes: Scientific and Practical Applications", Science, vol. 271, no. 5245, pp. 43–45, Jan. 5, 1996. Hybrid bilayer membranes or selectively tethered bilayer membranes may be more preferred as such membranes may have greater stability over time and therefor provide greater shelf lifetimes for sensor applications.

Bilayer membranes can be formed upon a planar oxide substrate, e.g., by initially forming vesicles followed by vesicle fusion or spreading of, e.g., phospholipid, bilayers on glass substrates as is well known to those skilled in the art.

In the present invention, a general fluorescence transduction method sensitive to multivalent binding can be used for detection of a selected toxin. The transduction method can achieve an agent-free assay that is fundamentally different from prior competitive-binding assay methods based on fluorescence quenching of ligands held in close proximity by multivalent receptors. In one embodiment, the present invention couples a specific multivalent reaction between toxins and receptors with distance-dependent fluorescence self-quenching of a fluorescent dye such as fluorescein. Such a transduction method possesses many advantages including relatively high chemical and functional stability of the receptors and of the transduction element, high specificity and enhanced sensitivity. Also, the transduction method of the present invention may allow for on-line measurement and remote sensing using optical fiber techniques. The key advantage of directly coupling recognition and signal transduction is the amplification of specific versus nonspecific binding events.

In one embodiment of the triggered optical biosensor, binding of a pentavalent cholera toxin protein will bring two or more of the tagged receptor molecules, e.g., tagged GM1 or the like, into close proximity thereby quenching their fluorescence that is excited using visible light.

Cholera toxin (CT) and ganglioside GM1 are a well-characterized recognition pair. CT consists of one A sub-unit responsible for catalysis, and five B sub-units, which define the binding region. Toxicity is initiated by the recognition and binding of B sub-units to a pentasaccharide moiety of GM1 in the cell surface followed by a mechanism involved in the entry of an A sub-unit through the membrane into the cell.

In one embodiment of the present invention, the transduction element used is fluorescein, which has a high extinction coefficient, a high fluorescence quantum yield and proximity-dependent fluorescence self-quenching. Other suitable fluorescent dyes are well known to those of skill in the art. Fluorescein can be covalently attached to the free amino group of lyso-GM1 by coupling lyso-GM1 with 5-(and 6-)-carboxyfluorescein, succinimidyl ester, in a mixing solvent of dimethyl formamide (DMF) and $Na_2CO_3$ buffer (pH=7.4) to produce a fluorescein-labeled GM1 as seen in FIG. 2. Lyso-GM1 is a GM1 molecule as shown in FIG. 2 where R is hydrogen. The GM1 molecule (ganglioside GM1) is where R is $CH_3(CH_2)_{16}CO$—. The fluorescein should have minimal influence on the binding affinity of the pentasaccharide moiety of GM1 to CT as the binding strength originates mainly from the hydrogen bonding located on sugar moieties and the fact that the two alkyl chains act as an anchor on the membrane surface. Strong fluorescence (excited at 498 nanometers (nm) and monitored at 520 nm) without self-quenching is observed for F-GM1 dissolved in tris-buffer (pH=8.0, [F-GM1]<=50 nanomoles (nM)) or distributed in the outer surface of the vesicles of palmitoyl, 9-octadecenoylphosphatidycholine (POPC) ([POPC]/[F-GM1]>=200). This indicates that F-GM1 is homogeneously distributed with no aggregation.

Figure 4:
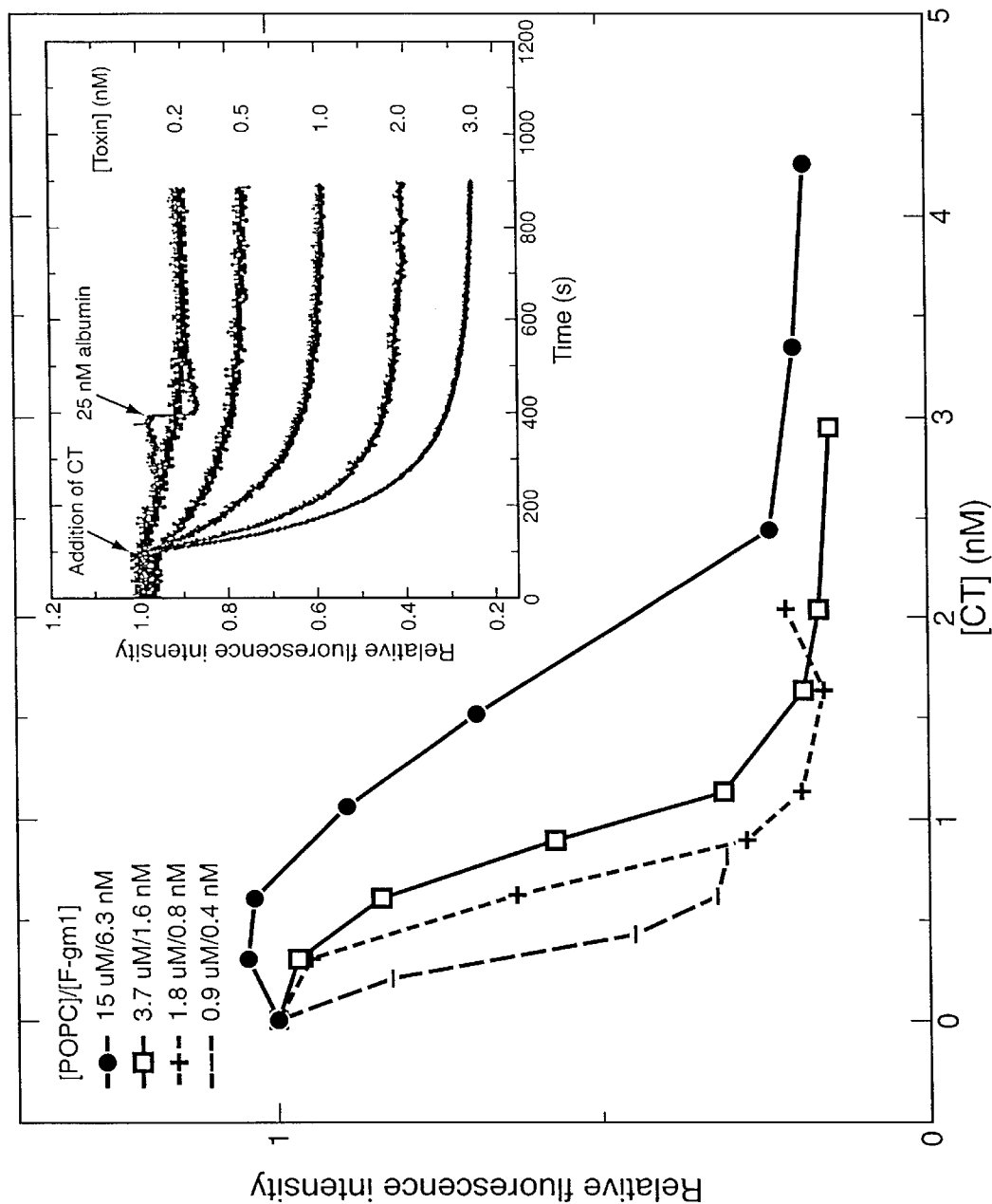
FIG. 4 shows a graph illustrating relative fluorescence of F-GM1 in POPC vesicles as a function of cholera toxin (CT) concentration.

The strong fluorescence was seen to decrease dramatically upon the addition of CT while the degree of fluorescence quenching depended upon the concentrations of both CT and F-GM1 as seen in FIG. 4 for F-GM1 in the outer surface of POPC vesicles. In tris-buffer, similar results have been observed. The detection limit can easily reach an order of 100 picomolar using conventional fluorimeter (a SPEX Flurolog-2 Spectrofluorimeter). In contrast, a much smaller fluorescence decrease is observed for the interaction of the F-GM1 in POPC vesicles and tris-buffer with a relatively high concentration of albumin. Comparison with flow cytometry results obtained with a labeled CT and unlabeled GM1 in POPC bilayers coated on the surface of glass beads showed little difference in binding affinity. This demonstrates that the high specificity of the binding between the pentasaccharide moiety and CT is not significantly affected by the labeled fluorescein. The binding reaction of F-GM1 with B sub-unit of CT was also investigated and similar results were obtained.

The fluorescence decrease was attributed to the self-quenching due to the close proximity of fluorescein fluorophores of F-GM1 brought by the multivalent toxin. Addition of an excess of CT into F-GM1 in tris-buffer or POPC vesicles resulted in a smaller decrease of fluorescence due to the formation of more monovalent complexes at the expense of multivalent complexes. For instance, addition of 2 nM CT in 2 nM F-GM in POPC vesicles (10 uM) resulted in a 80% decrease in fluorescence intensity while 100 nM CT caused only a 40% decrease. Based on crystal structure, the pentameric saccharide has a diameter of ~60 Å and a central pore of ~20 Å wide. The binding of F-GM1 to CT should bring fluoresceins within a critical self-quenching distance of ~50 Å for fluorescein. The present invention also provides a convenient method to investigate the multivalent interaction between receptors and toxins, such as real time kinetics and binding affinity in both homogeneous solution and in a biomimetic surface of lipid vesicles.

Figure 5:
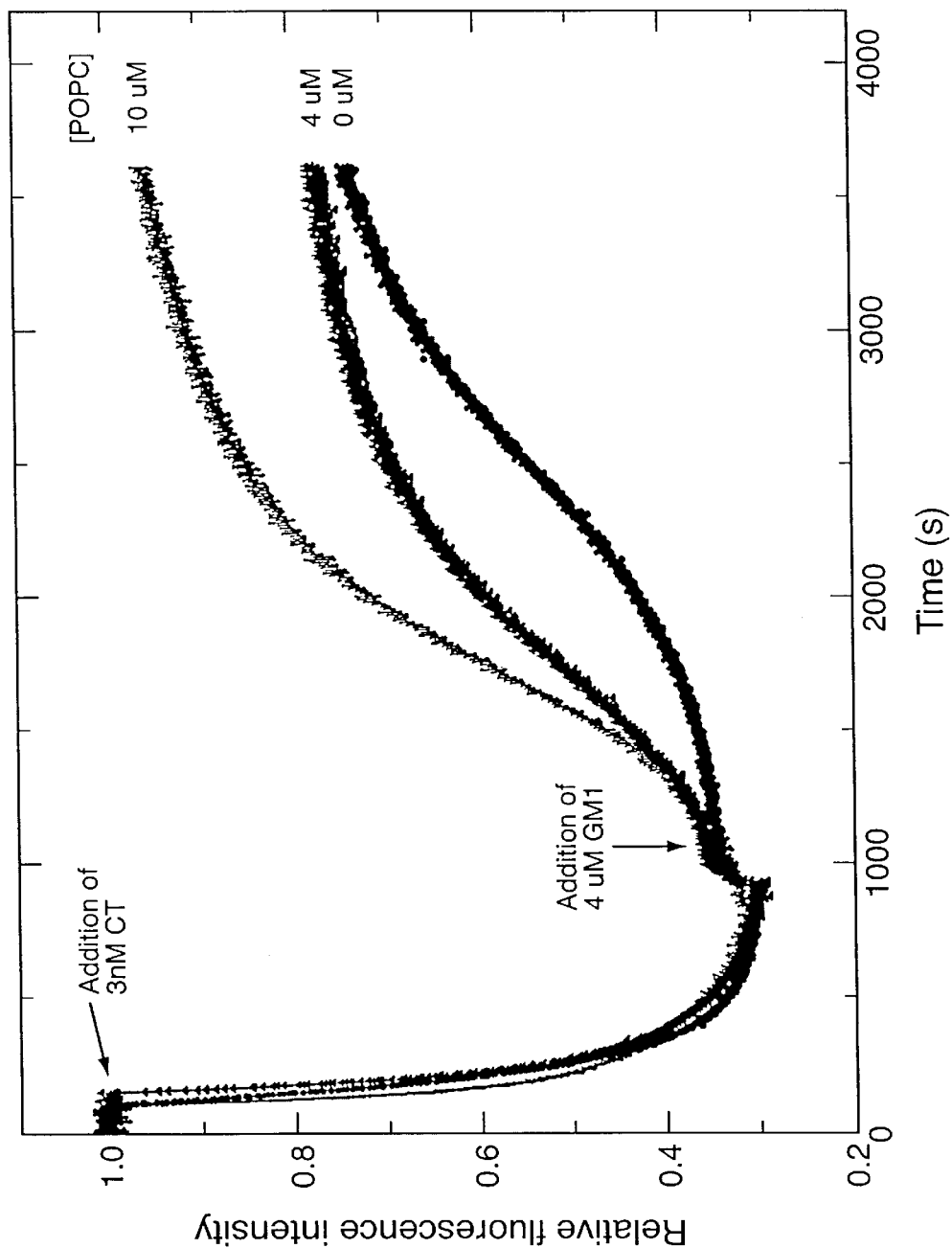
FIG. 5 shows a graph illustrating fluorescence change of F-GM1 in aqueous solution and the surface of POPC vesicles upon addition of cholera toxin and GM1.
Figure 6:
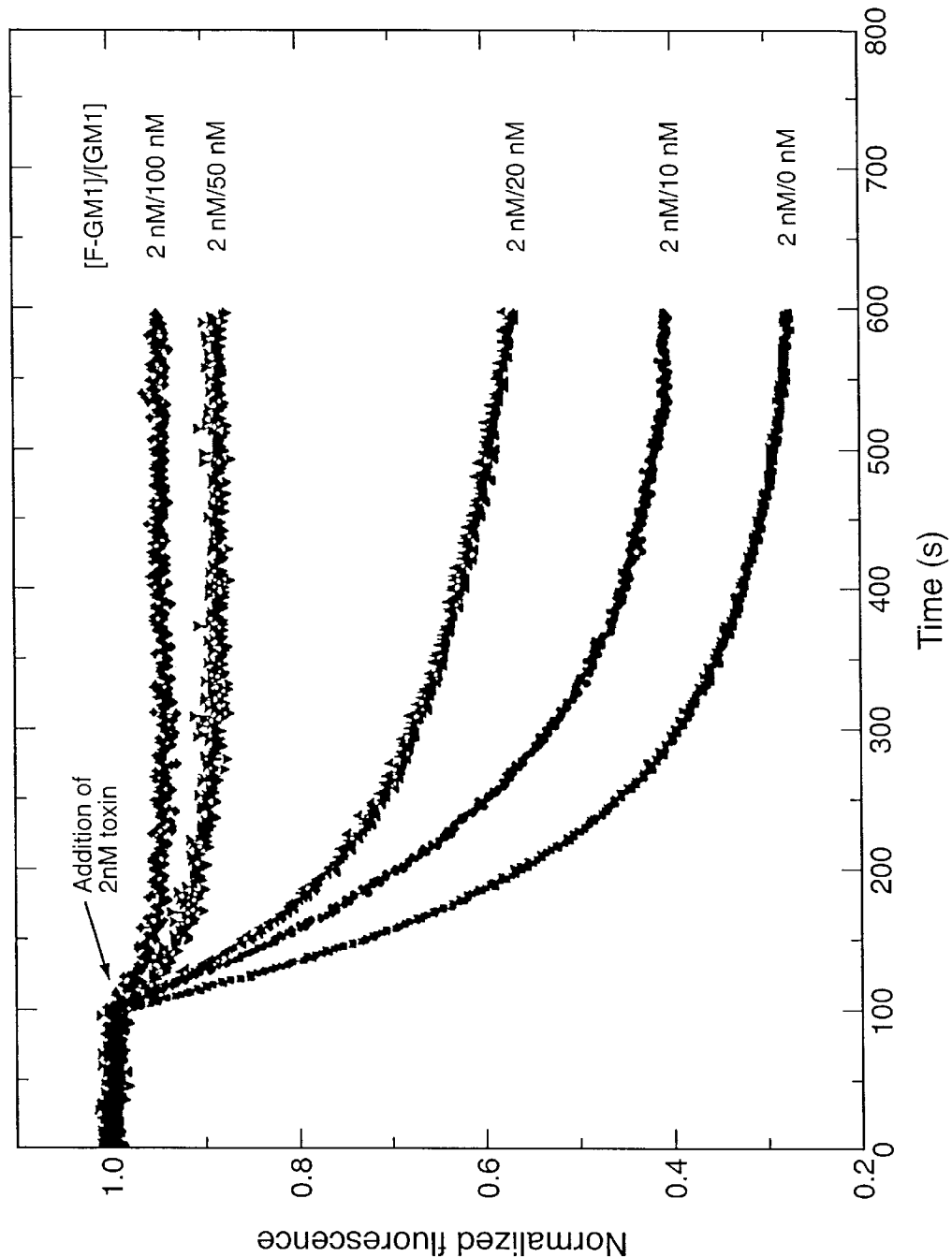
FIG. 6 shows a graph illustrating competitive binding of cholera toxin with F-GM1 and GM1 in POPC vesicles.

These results can thus allow for near-real time optical biosensors for toxins with high sensitivity and specificity. The labeled F-GM1 bound to toxins can be regenerated by inducing toxin dissociation via addition of unlabeled GM1 as seen in FIG. 5. The regeneration mechanism and kinetics of F-GM1 are complicated and likely determined by many factors such as the aggregation of GM1, incorporation of GM1 into lipid bilayers and lateral diffusion. Toxin dissociation from F-GM1 is much slower than the association due to the multivalent nature of binding. This is consistent with the results obtained by other techniques. The kinetics of the displacement of F-GM1 by GM1 depends on the concentration of POPC vesicles. Competitive binding of CT with F-GM1 and GM1 in the biomimetic surface of POPC vesicles is seen in FIG. 6. As expected, the presence of GM1 inhibits the binding of CT to F-GM1 to result in a smaller decrease of fluorescence. Similar competitive binding is observed for CT with F-GM1 and GM1 in tris-buffer solution.

Thus, the fluorescence self-quenching mechanism as a transduction method can be applied to take advantage of multivalent binding for detection through a receptor-protein interaction and other types of multivalent interaction. The present invention can be very flexible and sensitive, and can be used in a wide range of applications for detection of toxins and other molecules in both homogeneous solutions and the biomimetic surfaces of vesicles. The technique of the present invention should work using monolayers, bilayers and multilayers immobilized on substrates such as microspheres and other solid surfaces to act as a sensitive optical biosensor. Moreover, multivalent receptor ligands can be replaced by monovalent co-receptor in application to other recognition ligands (e.g. RNA, DNA or polypeptides).

The sensitivity or detection limit for cholera toxin protein has been found to be sub-nanomolar and the specificity, as measured using albumin as a competitive molecule for the biosensor, has been found to be high.

In another embodiment of the present optical biosensor, lyso-GM1 can be functionalized with either an acceptor dye molecule or a donor dye molecule whose excitation spectra overlap for efficient energy transfer. In effect, excitation of a blue emitting dye can result in fluorescence with a maximum at roughly 570 nm when functionalized GM1 is free to move about in the bilayer membrane. Upon exposure to a pentavalent cholera toxin, both the donor and the acceptor dyes are brought into close proximity. This can result in an energy transfer and a decrease in the fluorescence at 570 nm and a concomitant increase in the fluorescence of the acceptor dye that has its fluorescence maximum at roughly 630 nm. Such a simultaneous increase in the red fluorescence and decrease in the blue fluorescence is a highly distinguishing feature of this sensor approach. In effect, a two-color fluorescence measurement can be used to probe the intensity of fluorescence from both dye molecules. Only a specific binding event between the cholera toxin and the GM-1 receptor will give rise to such a simultaneous increase in one fluorescent signal with a decrease in the other. Any change in the environment will give rise to shifts of the fluorescence of both dye molecules. Such an energy transfer approach provides a means for self-referencing in biosensor applications.

As signal transduction is tied directly to a recognition event, non-specific binding where, for example, protein molecules attach the surface of the bilayer membrane, will not result in any signal. As a result, the amplification of the signal by the fluorescence effort, where many photons are emitted per unit time, results in an enhancement of both the sensitivity and specificity of the detection. In effect, the specific recognition event between the receptor and a protein, e.g., a protein toxin, triggers both optical transduction and amplification. Thus, the detection limits for such a sensor can be exceptionally high, e.g., the limit of detection can be better than 0.05 nano-molar. In similar fashion, the specificity is high, as evidenced in this case by the lack of any response to exposure to albumin at concentrations greater than 1000 times that of the cholera toxin. A critical aspect of the high specificity of the present sensor can be the use of hydrophobic dye molecules that reside in the upper leaf or portion of the bilayer membrane rather than exposed at the surface where non-specific interactions occur.

Another embodiment of the present invention involves use of structure-function dependent properties of cell surface receptors targeted by biological toxins to obtain a general, reagent-free, highly sensitive and specific sensing technology for effective detection of toxins. This method may meet the requirements for a wide variety of field and laboratory uses.

The present invention represents a triggered optical biosensor where mobility of optically tagged receptors in the upper leaf (layer) of a bilayer membrane can be used to trigger a two-color optical fluorescence change upon protein binding.

Figure 7:
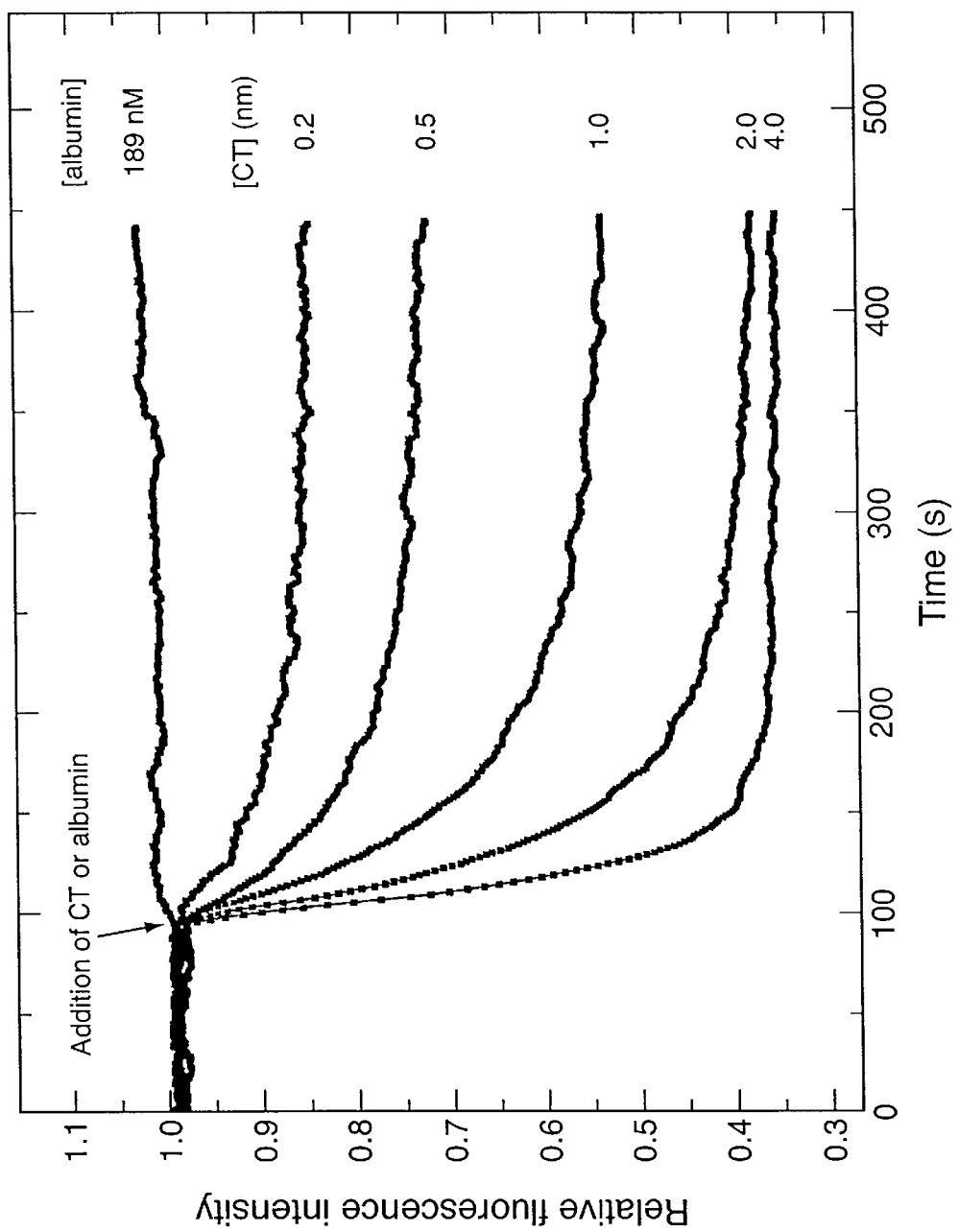
FIG. 7 shows a graph illustrating the fluorescence intensity change of 4,4-difluoro-5-(4-phenyl-1,3-butadienyl)-4-bora-3a,4a-diaza-s-undacene-3-propionic amide-lyso-GM1, (B5-GM1) in the outerlayer of POPC bilayers on glass beads upon addition of cholera toxin (CT) or albumin.

The recognition pair of the cell surface receptor, gangalioside GM1, and cholera toxin (CT) were chosen for initial studies because of its experimental accessibility and common features of bacterial toxins. The important feature of the receptor-toxin interaction (saccharide-protein interaction) is polyvalent binding where, for example, up-to-five receptors can bind for each CT molecule. The polyvalency amplifies the intrinsic affinity of monovalent saccharide ligands with proteins. The receptors in the cell surface are mobile and can laterally diffuse to accommodate the spatial requirement for the polyvalent binding. One embodiment of the present invention covalently attaches a fluorophore to the amino functionality of lyso-GM1 through an amide bond as a fluorescence transduction element (FIG. 2). Structural modification in this hydrophobic portion of the receptor should minimize the perturbation for the binding affinity and specificity of the native GM1 with CT since the fluorophore is far away from the pentasaccharide recognition moiety. The fluorophore-labeled receptor can be asymmetrically incorporated into a biomimetic membrane surface, either the outer layer of the preformed vesicles of phospholipids such as palmitoyl, 9-octadecenoyl phosphatidylcholine (POPC) or the lipid bilayer on supporting glass beads. Bilayer membrane surfaces can retain the dynamic (fluid phase at room temperature) and structural properties of a cell membrane so that the labeled receptors can maintain their mobility in the membrane surfaces. The fluorophores are carefully chosen, depending on the signal reporting mechanism of the binding events. Two types of transduction methods, distance-dependent fluorescence self-quenching and Förster-type energy transfer, are applied to take advantage of the polyvalent binding nature and the high mobility of the labeled receptors in the membrane surface (shown in FIG. 7).

Figure 8:
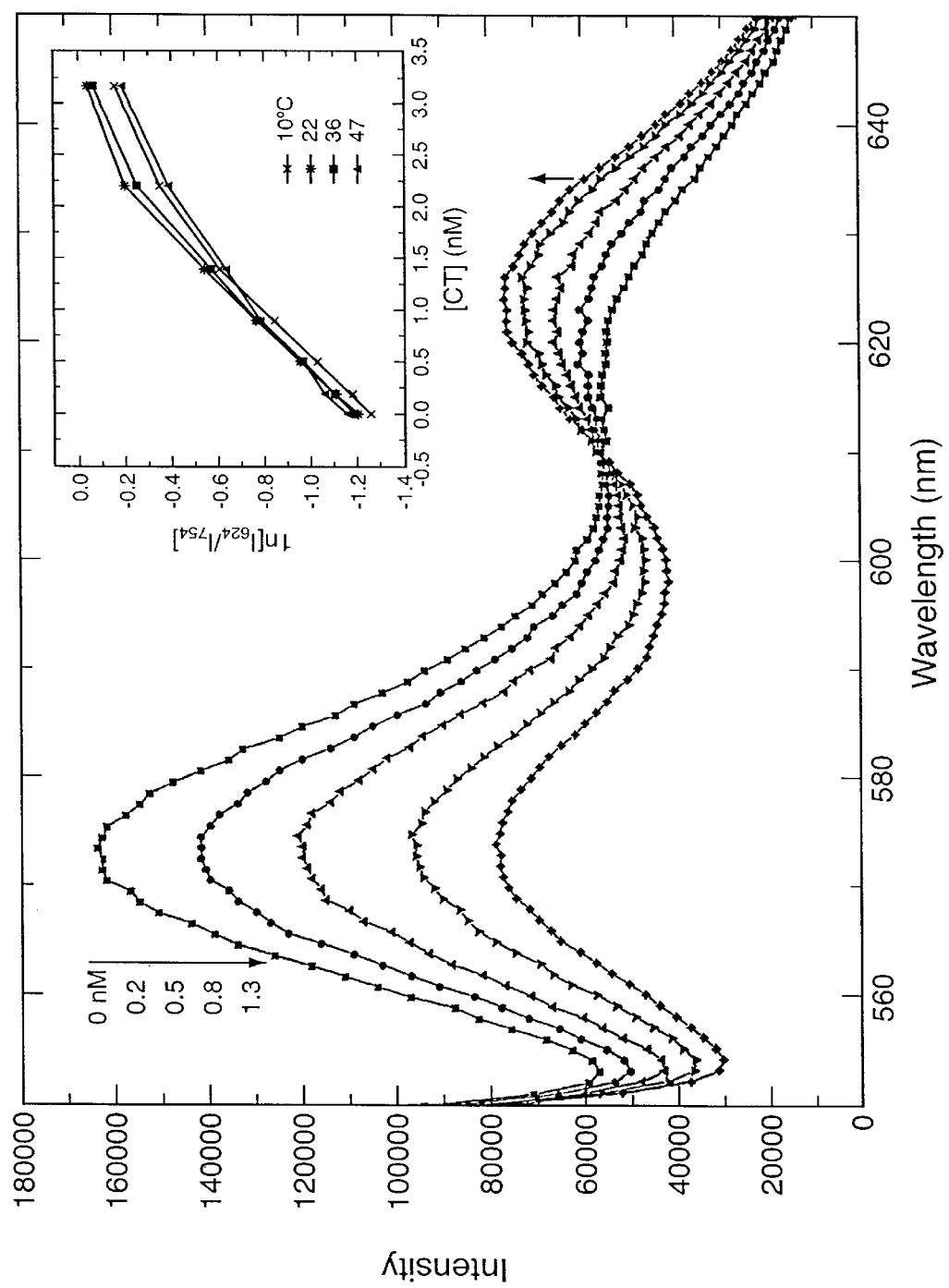
FIG. 8 shows a graph illustrating the fluorescence spectra of BTR-GM1 and RTMR-GM1 in the outerlayer of POPC bilayers on glass beads with different concentrations of cholera toxin (CT).

Optical detection of CT based on the fluorescence self-quenching of fluorescein covalently tethered to lyso-GM1 was described previously above. Although high sensitivity and moderate specificity (for example, against albumin) for signal transduction was achieved, fluorescein tagged GM1 was not stably incorporated into a membrane surface due to the ionic nature and water solubility of the fluorescein. Another drawback was its pH dependent fluorescence. In order to overcome the pH-dependence of its fluorescence and high water solubility of fluorescein, a neutral, hydrophobic BODIPY fluorophore with large extinction coefficient at long wavelength (584 nm) and high fluorescence quantum yield (close to unity) has been used to replace the fluorescein with an achievement of similar detection sensitivity and much higher specificity against albumin. A lower-end detection limit of 0.05 nM (nano molar) can easily be reached. B5-GM1 was found to be stably and homogeneously incorporated in the membrane surface and the polyvalent binding of CT to the labeled receptors was found to bring the attached fluorophores into proximity for an efficient fluorescence self-quenching (shown in FIG. 8). Under the conditions that 2 nM CT induces more than 70% decrease in fluorescence intensity, no non-specific binding signal was observed for albumin of up to 1,000 nM. The detection range and sensitivity depended upon the concentration of the labeled receptor. Sensitivity was higher with low concentration of the labeled receptor while the detection range became larger with higher concentration of the labeled receptor. While not wishing to be bound by the present explanation, it is believed that while the fluorescein in the fluorescein-labeled GM1 may stick out the surface to allow the interaction with albumin, the BODIPY fluorophore in B5-GM1 is believed to be buried in the hydrophobic portion of the membrane, which prevents any contact of the fluorophore with the hydrophobic pockets of the albumin. Also found was that, while the samples with a ratio of [POPC]/[B5-GM1] ranging from 200 to 2,000 show a large percentage drop (ca. 70%) in fluorescence intensity, the samples with the ratio larger than 20,000 show only small decrease (less than 10%) with CT. The small drop in fluorescence was attributed to two things: first, the surface density is too low to have efficient multivalent binding due to the affinity limitation; second, each vesicle does not have enough receptors available for the polyvalent binding. The fluidity of the membrane surface was also found to be critical for the mobility of the labeled receptors as demonstrated by the fact that the decrease (50%) in fluorescence intensity for B5-GM1 (10 nM) in the outer layer of dipalmitoylphosphatidylcholine vesicles (20 (M, Tc=42° C.) at 45° C. with 3 nM CT is much larger than the drop (20%) at 22° C.

The fluorescence self-quenching of B5-GM1 achieved remarkable success in terms of high sensitivity and specificity as well as the high chemical and functional stability of the labeled receptors. The fluorescence energy transfer was even more extraordinary. Receptors were covalently labeled with a fluorescence energy transfer pair, 6-((4,4-difluoro-1,3-dimethyl-5-(4-methoxyphenyl)-4-bora-3a,4a-diaza-s-indacene-2-propionyl)amino)hexanoic amide-lyso-GM1, (BTMR-GM1) (donor) and 6-(((4-(4,4-difluoro-5-(2-thienyl)-4-bora-3a,4a-diaza-s-indacene-3-yl)phenoxy)acetyl)amino)hexanoic amide-lyso-GM1, (BTR-GM2) (acceptor), and incorporated together into the outer layer of either POPC vesicles or POPC bilayers on glass beads. Both fluorescence donor and acceptor have sharp absorption spectra with high extinct coefficient and high fluorescence quantum yields, and can stably be incorporated into the phospholipid bilayers. FIG. 4 shows the fluorescence spectral change upon addition of different concentrations of CT. The fluorescence intensity (peak at 624 nm) of the acceptor increases at the expense of the fluorescence intensity (peak at 574 nm) of the donor. Without CT, the donor-labeled GM1 and acceptor-labeled GM1 with the ratio of [POPC]/[receptors]>200 are distributed homogeneously in the membrane surface and fluoresce independently. Each CT can bring five receptors within a relatively short distance for an energy transfer to occur and possibility of the presence of both donor-labeled and acceptor-labeled receptors in one complex should be high. The samples with different ratio (from 0.25 to 4.0) of [BTMR-GM1]/[BTR-GM1] shows similar results. As shown in FIG. 4 (inset), ln[I624/I574] has a linear relationship with the concentration of CT within the upper detection limit (approximately one fifth of the total labeled-receptor concentration, which is consistent with the five binding sites of each CT and almost all the receptors bind to the CT). As in the case of fluorescence self-quenching, the detection sensitivity and dynamic range in the energy transfer case can also be adjusted by the total concentration of the labeled-receptors. Lower concentration of the labeled receptors gives higher sensitivity but smaller detection range. Less than 0.05 nM of CT can be reliably detected using conventional fluorimeter (a SPEX Flurolog-2 Spectrometer) with a response time of less than five minutes. The parameter ln[I624/I574] starts to level off when [CT] is more than one-fifth of the total receptor concentration (upper detection limit for each specific sample) or up to 5 times of the upper detection limit. Then, the parameter starts to drop slowly to 40% from its highest point with further addition of CT up to 400 times higher in concentration than the detection limit. The parameter drop is reasonably attributed to the formation of monovalent complexes due to the presence of excess of CT. As expected by the fact that the hydrophobic fluorophores should anchor in the interior of the membrane, high concentration of albumin (more than one thousands times higher than the detection limit) caused no change in the fluorescence spectra due to the protection provided by the bilayer against nonspecific interaction between albumin and the fluorophore.

Such a detection scheme using two signals of two transduction elements with similar photophysical properties has a huge advantage over single signal systems and shows little temperature dependence ranging from the tested temperature of 10° C. to 47° C. (inset of FIG. 4). The small temperature dependence can be understood by the fact that the parameter (ln[I624/I574) is taken from two similar fluorophores and they act as an internal reference to offset any absolute intensity change caused by temperature variation or possibly other environmental changes. Another advantage of the distance-dependent signal transduction over techniques based on changes in the index of refraction, such as surface plasmon resonance spectroscopy, is its silence to the nonspecific binding of toxin itself to the membrane surfaces. Unlike B5-GM1, samples with only BTR-GM1 or BTMR-GM1 incorporated in the outer layer of POPC vesicles or POPC bilayers on glass beads showed only a small decrease in fluorescence intensity (less than 15%) upon addition of even excess CT. Apparently they do not exhibit significant fluorescence self-quenching under these circumstances.

For both fluorescence self-quenching detection using B5-GM1 and the energy transfer scheme using BTMR-GM1 and BTR-GM1, the original fluorescence spectra can be fully recovered by addition of excess of unmodified GM1 to compete off the labeled receptors. This competing process takes more than 10 hours with much higher concentration of GM1 than the labeled receptors in the presence of POPC vesicles or bilayers on glass beads. This is expected due to the slow asymmetric incorporation process of GM1 in the form of micelles into the outer layer of POPC bilayers before the competitive binding occurs. It is expected that the protein toxin binding to optically tagged receptors can also be reversed by flowing solutions that denature the protein without degradation of the receptor-membrane structure. Particularly so, if more stable hybrid bilayers are employed along with selective covalent attachment of anchoring groups that span the entire bilayer. Thus, it should be possible to fabricate robust membrane platforms that can be reused for near real-time detection.

The receptor-toxin recognition pair coupled with the energy transfer and fluorescence quenching optical transduction techniques of the present invention provide a general method for the effective detection of multivalent interactions and, in particular, protein toxins. The essential elements for this approach include the construction of a biomimetic membrane surface that contains the optically labeled recognition molecules, species-specific multivalent binding and signal transduction and amplification that is triggered by the binding event. Such a direct, reagent-free assay with high sensitivity, specificity and stability of the receptors and the membrane should find application in laboratory and field diagnostics and sensing of selected biological toxins and pathogens.

Recent advances in building stable biomimetic phospholipid bilayers make it practical to fabricate robust miniaturized multi-element sensor array systems based on techniques of the present invention coupled with fiber optic or waveguide technologies. Different biosensors within a multi-element array can be used to target different biomolecules. Suitable waveguides can be single channel or multiple channel. Moreover, the present invention can be readily adapted to flow cytometry techniques which are already built, e.g., into the nations Biological Integrated Defense System (BIDS).

Carbohydrate-protein interactions have recently attracted attention due to the increasing realization of their importance in cell functions and their unique yet intriguing interaction. Although monosaccharide-protein interaction is relatively weak, high affinity and specificity of protein-carbohydrate interaction are achieved through cooperative mulitvalent binding. Multivalency can be established by several possible ways, either alone or together: (a) ligand multivalency; (b) an extended binding region capable of interaction with more than just a single monosaccharide residue of an oligosaccharide; (c) subunit multivalency— clustering of several identical binding sites by formation of protein oligomers or a protein with multiple binding subunits. For example, concavalin A and peanut lectin with four subunits, each having a binding site, bind selectively with glucose (and manoside) and galactose, respectively, through type (c), while cholera toxin with five subunits binds strongly with pentassacharide of GM1 through both type (b) and (c). The type (a) interactions have been used to design bioassays for detection of both carbohydrates. Two general optical transduction methods for detection of multivalent proteins (specifically CT) by taking advantage of type (c) interaction between carbohydrate and proteins are described. An optical sensing method is coupled with type (c) interaction for detection of target proteins with multiple binding subunits. This method is expected to work for any interaction involved in coreceptors.

Three highly sensitive, specific and reagent-free optical detection methods for polyvalent proteins have been developed by direct coupling of distance-dependent fluorescence self-quenching or resonant energy transfer to the protein-receptor binding events. The receptors (e.g. ganglioside GM1) as recognition units for proteins such as cholera toxin (CT) were covalently labeled with fluorophores as signal transduction elements, and then incorporated into a biomimetic membrane surface. The presence of proteins with multiple binding sites (e.g. five binding sites for CT) for the receptors causes dramatic change for the fluorescence of the labeled receptors. In a first general scheme using fluorescence self-quenching as a transduction method, the fluorescence intensity drops significantly due to aggregation of the fluorophore-labeled receptors induced by the specific multivalent binding on a biomimetic surface. In a second general scheme, by labeling the receptors with a fluorescence energy transfer pair, the labeled-receptor aggregation results in a simultaneous decrease in donor and increase in acceptor fluorescence providing a unique signature for specific protein-receptor binding. In a third general scheme using the biomimetic surface as part of the transduction elements and combining both fluorescence self-quenching and energy transfer to enhance the signal transduction, a signal amplification was achieved for the detection of the multivalent interactions. The detection systems can reliably detect less than 0.05 nM CT with fast response (less than five minutes). Although developed for application to the detection of multivalent proteins, this approach can easily be adapted to any biosensor scheme that relies on multiple receptors or co-receptors. Besides the application for the protein detection, the methods can also be used to detect any small molecules involved in the multivalent bindings such as receptors and metal ions required for the interacton of some proteins (e.g. C-lectins) with ligands. The methods can also be applied to investigate the kinetics and thermodynamics of the multivalent interaction using either fluorimeter or flow cytometer.

In systems of the present invention, a bilayer of natural phospholipids (POPC) can be applied either in aqueous solution or on solid support to biomimic cell surface in which optically tagged receptors (GM1) can anchor and diffuse laterally. As described previously, the binding of protein (cholera toxin) brings more than one receptor and therefore the tagged fluorophores into a close distance to induce either fluorescence self-quenching or energy transfer. In this signal transduction method, a biomimetic surface of a synthetic, fluorophore-tagged phospholipid mixed with a natural phospholipid (POPC) is applied. In this case, the surface acts not only as a supporting surface but also a part of transduction elements. It is expected that the bilayers of the mixed phospholipids still gives a biomimetic surface with a fluid phase so that the fluorophore-labeled receptor anchored on the surface can be laterally mobile. The excimer of pyrene in the bilayers act as fluorescence donating group with the BODiPY covalently attached to the receptor as a fluorescence acceptor. The choice of pyrene as a fluorescence donor is its high tendency for the formation of excimer, which gives a relatively high quantum yield of excimer fluorescence with a large Stoke shift and long fluorescence lifetime. The significant overlap of the pyrene excimer fluorescence with the absorption spectra of DABCY and BF along with the long fluorescence lifetime of the excimer makes it possible that an efficient energy transfer from the excimer to both acceptors occurs. One acceptor molecule may quench the fluorescence of many donor molecules, so that signal transduction amplification can occur. When acceptor-tagged receptors are homogeneously distributed in the surface with donors in a proper percentage, a relatively weak fluorescence of the pyrene excimer should be observed due to the quenching by the acceptors. In the case of fluorescent acceptors, a strong acceptor fluorescence should be expected even though only the donor is excited. The aggregation of the receptors and thereafter the fluorescence acceptors caused by the multivalent bind of proteins will reduce the overall energy transfer efficiency with a consequence of an increase in excimer fluorescence, and a fluorescence decrease for the fluorescent acceptors such as 4,4-difluoro-5,7-dimethyl-4-bora-3a,4a-diaza-s-indacene-3-propionic amide-lyso-GM1, (BF-GM1). The schematic illustration of the signal transduction is shown in FIG. 1.

Figure 9:
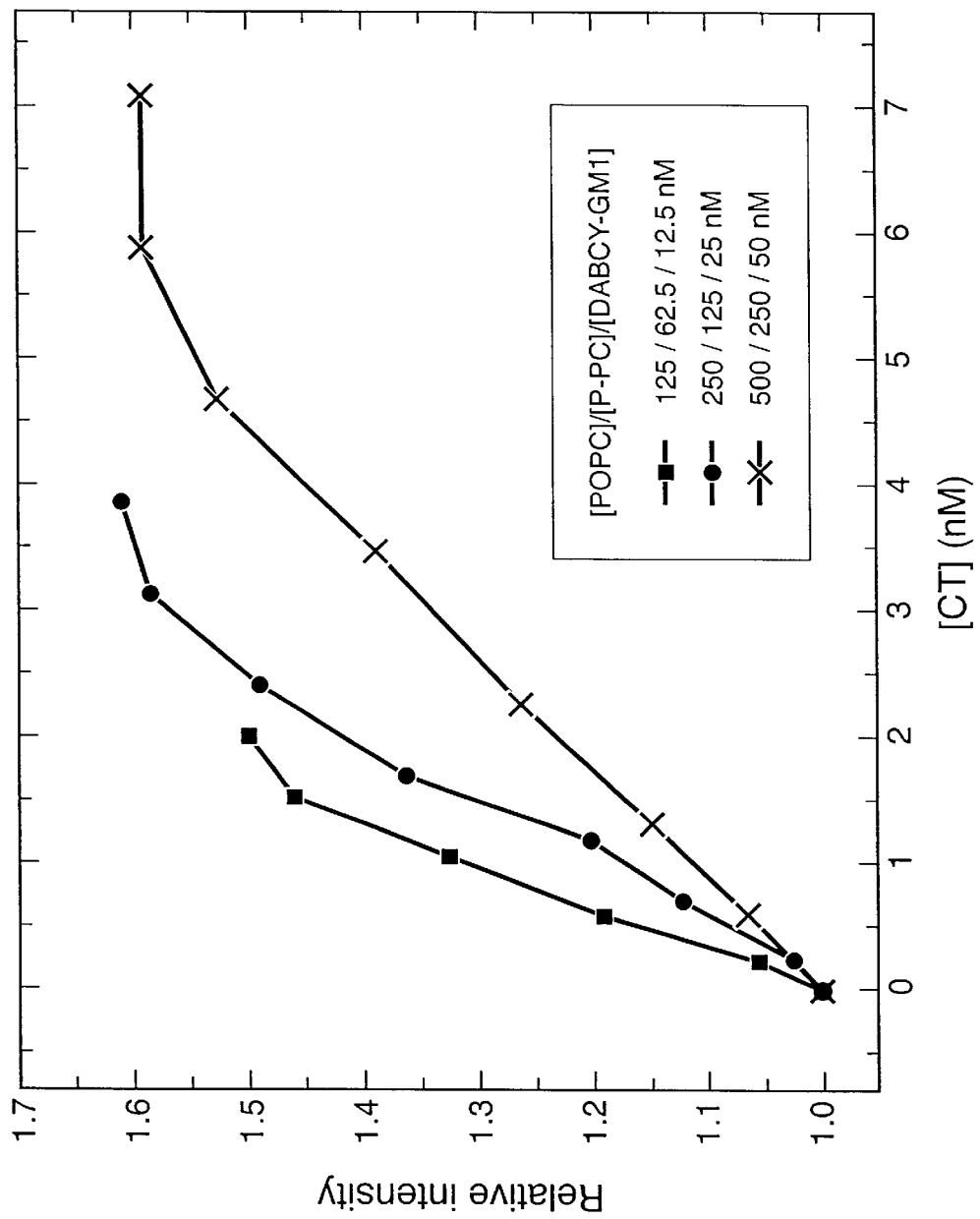
FIG. 9 shows a graph illustrating relative fluorescence intensity of pyrene excimer for POPC/P-PC bilayers with DABCY-GM1 in both leaflets of the bilayers as a function of cholera toxin concentration.

Bilayer vesicles of P-PC and POPC ([POPC]/[P-PC]=2/1 in most of cases) are used as a biomimetic surface, which is found to consist of a relatively high percentage of excimer when excited. The fluorescence intensity of the excimer at peak (482 nm) is more than twice large than the intensity of the monomer. Introduction of only 10% of nonfluorescent DABCY-GM1 (versus P-PC) into the outer layer of the bilayer surface causes 70% fluorescence of the excimer while more than 80% fluorescence of the excimer is quenched by only 5% DABCY-GM1 incorporated into the both sides of the bilayers. This result demonstrates the formation of an enclosed bilayer structure and efficient quenching of the excimers not only in the same layer but also the other layer although the efficiency is higher if both donor and acceptor are in the same layers. From the result of quenching versus percentage of the DABCY-GM1 in the bilayer surfaces, it is estimated that each DABCY can quench the excimer fluorescence of approximately 10 pyrene molecules if two thirds of pyrenes form excimers. In the case of DABCY-GM1 (10% versus P-PC) in the outer layer of the bilayer vesicles of POPC/P-PC (2/1), presence of CT induces a fluorescence increase of the pyrene excimer up to about 45%, while the excimer fluorescence increases up to about 60% with DABCY-GM1 in both sides of the bilayers with the same percentage. This is illustrated in FIG. 9. Similar to using fluorescence self-quenching of fluorescein and B5GM1, the sensitivity (less than 0.1 nanomolar (nM) for CT) and detection range depend on the concentration of DABCY-GM1 as well as the ratio of [POPC]/[P-PC]/[DABCY-GM1]. If the ratio of [POPC]/[P-PC] is too high, the percentage of pyrene to form excimer drops dramatically, while the background fluorescence before addition of CT is high for samples with low percentage of DABCY-GM1. Apparently, the excimer fluorescence does not fully recover because the aggregated acceptor can still quench the fluorescence of the excimers nearby. The advantage of this approach versus the distance-dependent self-quenching for the detection of multivalent proteins is the increase of the signals instead of decrease in the cases of self-quenching and potential of signal amplification achieved by the efficient energy transfer and high density of donor fluorophore in the surface. In order to test the selectivity of this sensing method, albumin is used as a reference. It is found that for a sample containing 0.25 micromolar (uM) POPC, 0.125 uM P-PC and 25 nM DABCY in both sides of the bilayers, 2.4 nM CT induces about 50% increase while 15.6 nM albumin causes about 12% increase. The possible cause for the relatively significant non-specific signal generation for the albumin is the interfering binding of the DABCY or pyrene moities with the hydrophobic pockets of albumin or perturbation of the bilayer structures that determine the efficiency of excimer formation. Construction of more stable bilayer should reduce such nonspecific signal generation.

Figure 10:
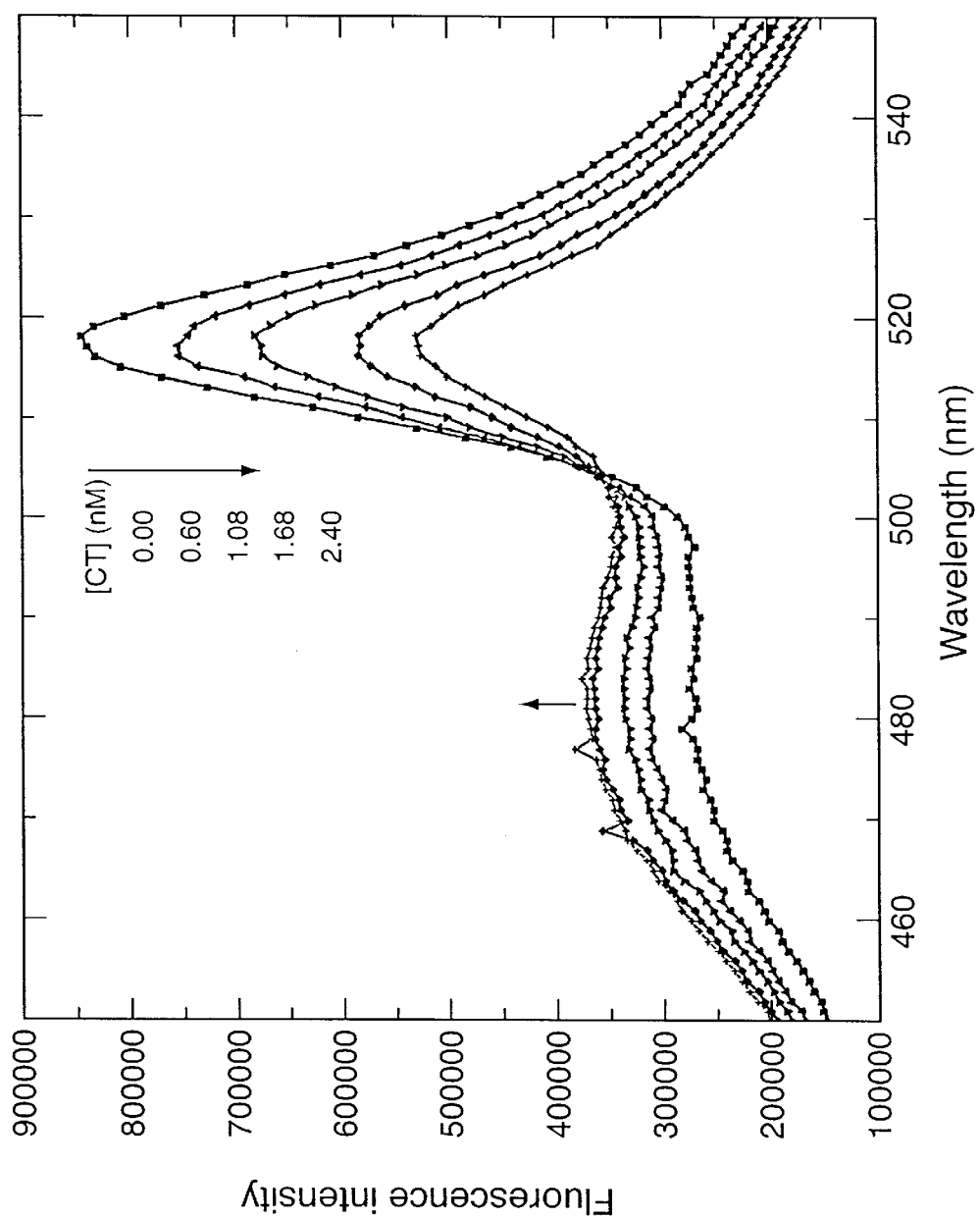
FIG. 10 shows a graph illustrating fluorescence spectra of a POPC/P-PC bilayer with BODIPY-FL-GM1 in the outer leaflet after addition of cholera toxin.

Unlike the case of non-fluorescent DABCY as a quencher, a simultaneous double color change can be achieved by using fluorescent acceptor covalently attached to GM1. When BF-GM1 (5% versus P-PC) is incorporated into the outer layer of POPC/P-PC=2/1 bilayers, a relatively weak fluorescence of pyrene excimer and strong fluorescence of BF-GM1 are observed even though only pyrene is excited. This is believed due to the energy transfer from the excimer to BF-GM1 as expected by the good overlap between excimer fluorescence and the absorption spectrum of BF-GM1. Addition of CT induces the aggregation of BF-GM1 in the bilayer surface. On one hand, the energy transfer from excimer to BF becomes less efficient to boost the excimer fluorescence, on the other hand, combination of less efficient energy transfer and distance-dependent self-quenching of BF itself contributes to the decrease of the emission (shown in FIG. 10). Again, higher sensitivity can be achieved with low concentration of BF-GM1, while large detection range with high concentration of BF-GM1.

In another embodiment of the present invention, flow cytometry is used in the biosensor system for the detection of the target multivalent biomolecules.

Flow cytometry represents a powerful and versatile tool for a wide variety of applications in biological studies. These applications include cell sorting, studies of DNA contents in cells, and examinations of ligand-receptor interactions. Its intrinsic capability to discriminate fluorescence molecules on the particle surfaces from free fluorescent molecules in the volume surrounding the particles provides quantitative fluorescence measurements of particle-bound ligands without need to wash away free ligands. The feature of the easily-constructed homogeneous assay format and continuous discrimination of free and bound ligands for flow cytometry are particularly useful for kinetic studies. Flow cytometry also permits multi-parameter measurements of individual cells or particles, which may allow simultaneous identification of multiple targets in a mixture to provide a potential high throughput screening techniques. The potential of flow cytometry as a biosensor platform for detection of protein toxins was therefore explored and found to be highly sensitive, selective and fast, as well as simple and easy to use.

The principles of using distance-dependent fluorescence self-quenching or fluorescence energy transfer or combination of both as signal transduction mechanisms to detect the multivalent interactions still apply. The above-described work was carried out using a conventional spectrofluorometer (SPEX Fluorolog 2 spectrofluorometer). Since these biosensor systems can be easily constructed on the surfaces of microspheres, they can be directly adapted to flow cytometry. One of the important advantages of flow cytometry over conventional spectrofluorometry is its high sensitivity as a result of its low background and high signal/noise ratio. Optimal parameters associated with the sensing surfaces of this biosensor system to achieve possibly highest sensitivity in a commercial flow cytometer was therefore sought. The factors which influence the bind kinetics were also studied. The knowledge of these parameters which play important roles in determining detection sensitivity and binding kinetics. The knowledge of these parameters which play important roles in determining detection sensitivity and binding kinetics are essential to construct a biosensing system with enhanced performance.

Palmitoyl, 9-octadecenoyl phosphatidylcholine (POPC), cholera toxin, human serum albumin and trizma base/acid for preparation of tris buffer (50 mM with pH=8.0 unless otherwise stated) were purchased from Sigma. Ganglioside GM1 and lyso-GM1 were obtained from Matreya Inc. (Pleasant Gap, Pa.). 4,4-difluoro-5,7-dimethyl-4-bora-3a, 4a-diaza-s-indacene-3-propionic acid ($B_{FL}$), succinimidyl ester and 4,4-difluoro-5-(2-thienyl)-4-bora-3a,4a-diaza-s-indacene-3-propionic acid ($B_{558/568}$), succinimidyl ester were purchased from Molecular Probes, Inc. (Eugene, Oreg.). Glass beads (5 μm in diameter) were purchased from Bang's Laboratories, Inc. (Fishers, Ind.). The labeling of lyso-GM1 with dyes activated with succinimidyl ester and the preparation of glass beads coated with POPC bilayers with the labeled GM1 in the outer leaflets were described above. The regular fluorescence measurements were recorded on a SPEX Fluorolog-2 spectrofluorometer. A Microscon Ultrasonic cell disruptor (SL2000, Misonix, Inc., NY) was used for probe sonication.

A FACStar Plus flow cytometer (Becton Dickinson (BD), Mountain View, Calif.) equipped with argon-ion lasers was used to measure forward angle light scatter, right angle light scatter, and fluorescence of the microspheres. These parameters were acquired as pulse height signals (four decades in logarithmic scale) in list mode for 5000 or 10000 events at a rate of about 200 cells per second. The samples were analyzed using the standard stream-in-air configuration, usually triggered on FCS as threshold parameter. The lasers were tuned to 488 mm at a power output of 500 mW. The emission of the acceptor and donor was measured with a 575 mm band pass filter (BD 575 DF 26), and a 530 mm band pass filter (BD 530 DF 30; both Becton Dickinson), respectively.

The record list-mode data files were transferred by FASTFILE-software (BD) to a PC-system. Data analysis and graphics were performed using the DAS-software package (DAS=Data Analysis Software (DAS V 4.03).

Figure 11:
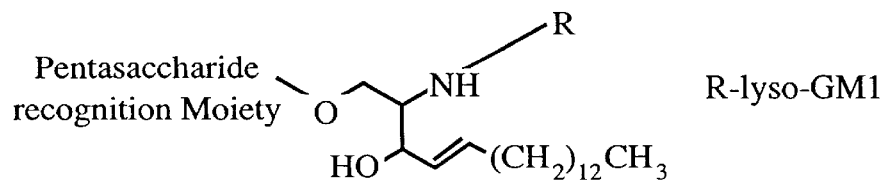
FIG. 11 shows chemical structures of additional labeling groups used to label ganlioside GM1 at the R site for use in the present invention.
Figure 11:
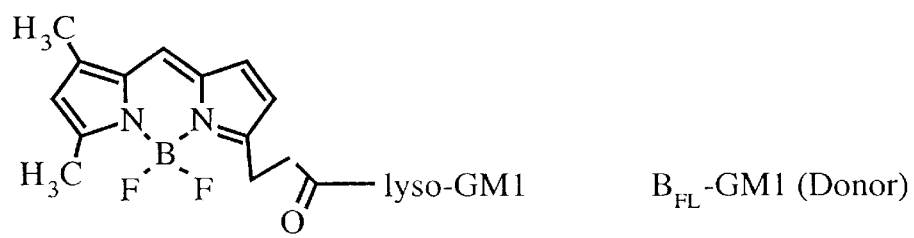
Figure 11:
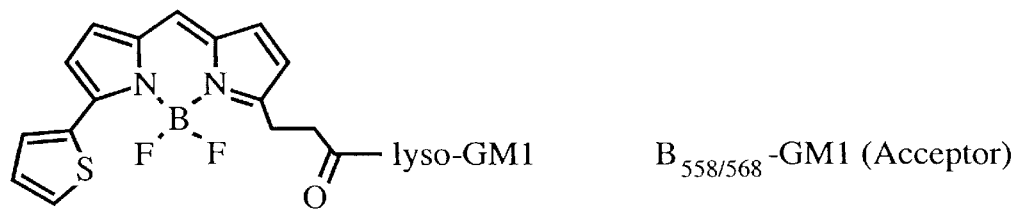

It was demonstrated above that a distance-dependent fluorescence energy transfer mechanism can be utilized as an optical signal transduction for selective detection of multivalent cholera toxin (CT). The biosensing system can achieve a simultaneous double color change that tremendously increases the detection sensitivity and reliability. Although the CT-induced energy transfer efficiency (29%) between BTMR (fluorescence donor) and BTR (acceptor) is relatively high as a result of the significant overlap between the fluorescence spectrum of BTMR and absorption spectrum of BTR, the optimal excitation wavelength for the energy transfer pair lies from 520 nm to 535 nm. In order for this biosensing system to be adapted to a commercial flow cytometer with an argon ion laser as excitation source (488 nm), a new energy transfer pair, $B_{FL}/B_{558/568}$–GM1 (FIG. 11) was identified, which provides an optimal excitation wavelength range from 480 nm to 510 nm.

Figure 12:
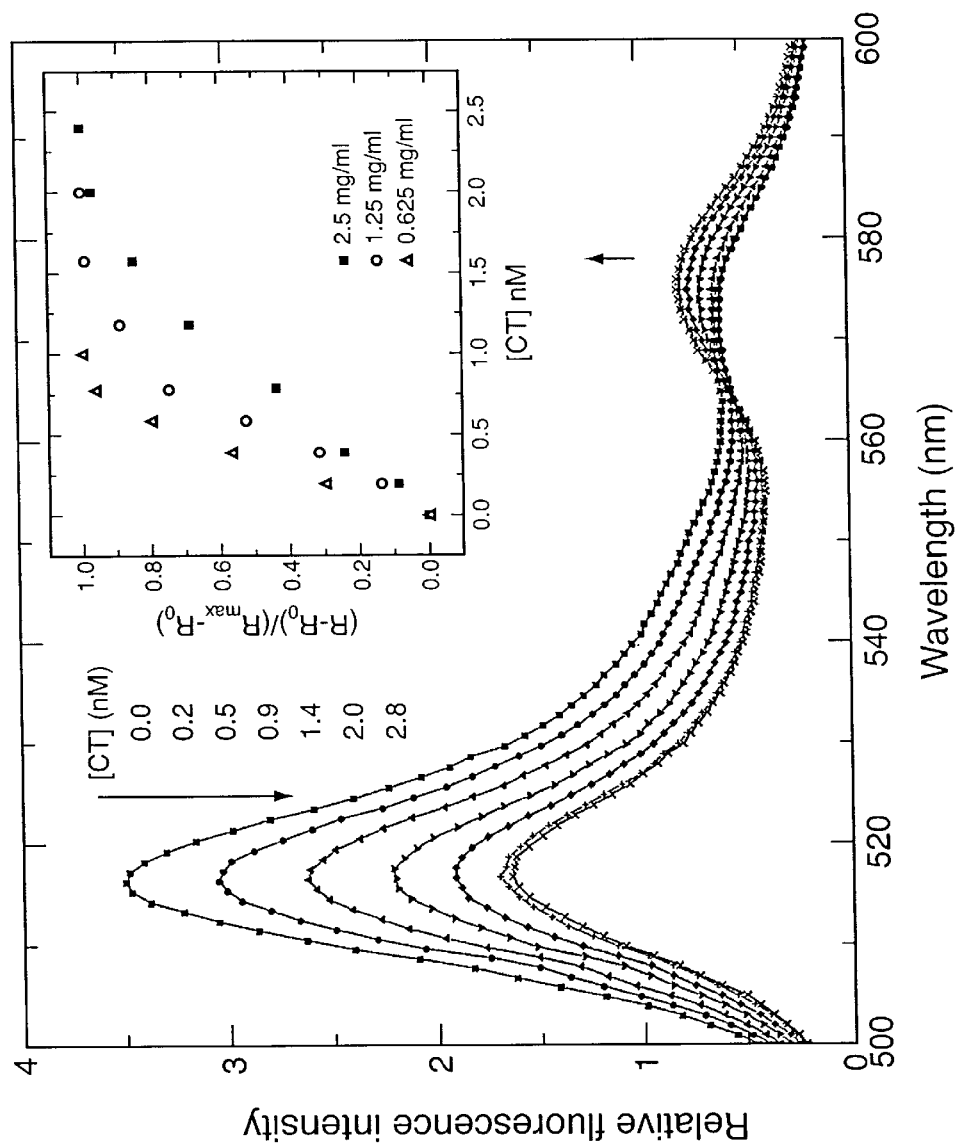
FIG. 12 shows a graph illustrating fluorescence spectra of $B_{FL}$-GM1 and $B_{558/568}$-GM1 in the outer leaflet of POPC vesicles in the presence of different amounts of cholera toxin and the inset illustrates a plot of $(R-R_o)/(R_{max}-R_o)$ versus cholera toxin concentration for samples containing different concentrations of beads coated with $B_{FL}$-GM1 and $B_{558/568}$-GM1 where R, $R_o$ and $R_{max}$ are the intensity ratio ($I_{624}/I_{574}$) of the two fluorescent peaks at 572 nm (for the acceptor) and 518 nm (for the donor) for samples with cholera toxin, samples without cholera toxin and samples with saturating concentrations of cholera toxin, respectively.

FIG. 12 shows the fluorescence spectra of a sample containing $B_{FL}$–GM1 and $B_{556/568}$–GM1 in the outer leaflet of POPC bilayers coated on glass microspheres in the presence of different concentrations of CT. Multivalent binding of CT with up to five labeled GM1 bring the fluorescence donor ($B_{FL}$) and acceptor ($B_{556/568}$) into a close proximity to trigger and energy transfer, the acceptor fluorescence increases at the expense of the donor fluorescence upon addition of CT. The plot of the normalized fluorescence change (ratio of the acceptor fluorescence intensity over the donor intensity) as a function of CT concentration (inset) show a nearly straight line within saturation concentration. The fluorescence change levels off when the cholera toxin concentration [CT] approaches or exceeds the saturation concentration (approximately one fifth of the total concentration of the labeled GM). When much excess of CT was added, the fluorescence change actually drops as a result of the formation of more low-valent complexes. Compared with the 29% CT-induced energy transfer efficiency for BTMR/BTR-GM1 pair, the CT-induced energy transfer efficiency (15%) for $B_{FL}/B_{558/568}$–GM1 is much lower owing to the smaller overlap between the fluorescence of $B_{FL}$–GM1 and absorption spectrum of $B_{558/568}$–GM1. Consistent with above results, the detection sensitivity and dynamic range can be easily adjusted by the number of the labeled receptors available for CT binding. The plot of the fluorescence change versus [CT] for a sample (200 ul) containing 0.025 mg beads coated with POPC bilayers and labeled GM1 had a sharper slope and leveled off at lower concentration than that for a sample (200 ul) containing 0.1 mg beads. In spite of its low energy transfer efficiency, the system can still reliably detect less than 100 pM CT using commercial fluorometer.

As demonstrated above, the detection method using energy transfer mechanism to achieve a simultaneous double-color changes has a huge advantage over the scheme utilizing a single color change in terms of detection reliability and sensitivity. Although the absolute fluorescence intensities of both donor and acceptor are often sensitive to environmental perturbations such as temperature and polarity changes, the ratio of the fluorescence intensities of two similar fluorophores in the same environment should to some extent immune to such perturbations. For this current system, it was found that, whereas the absolute fluorescence intensities of both donor and acceptor slightly decrease when the sample was heated from 10° C. to 50° C., the plots of the fluorescence intensity ratio versus [CT] were almost identical for the temperature range tested. Significant changes in pH (from 5.0 to 10.0) and ionic strength (0 mM to 0.5 M of NaCl) in the samples had no influence on the detection results.

Figure 13:
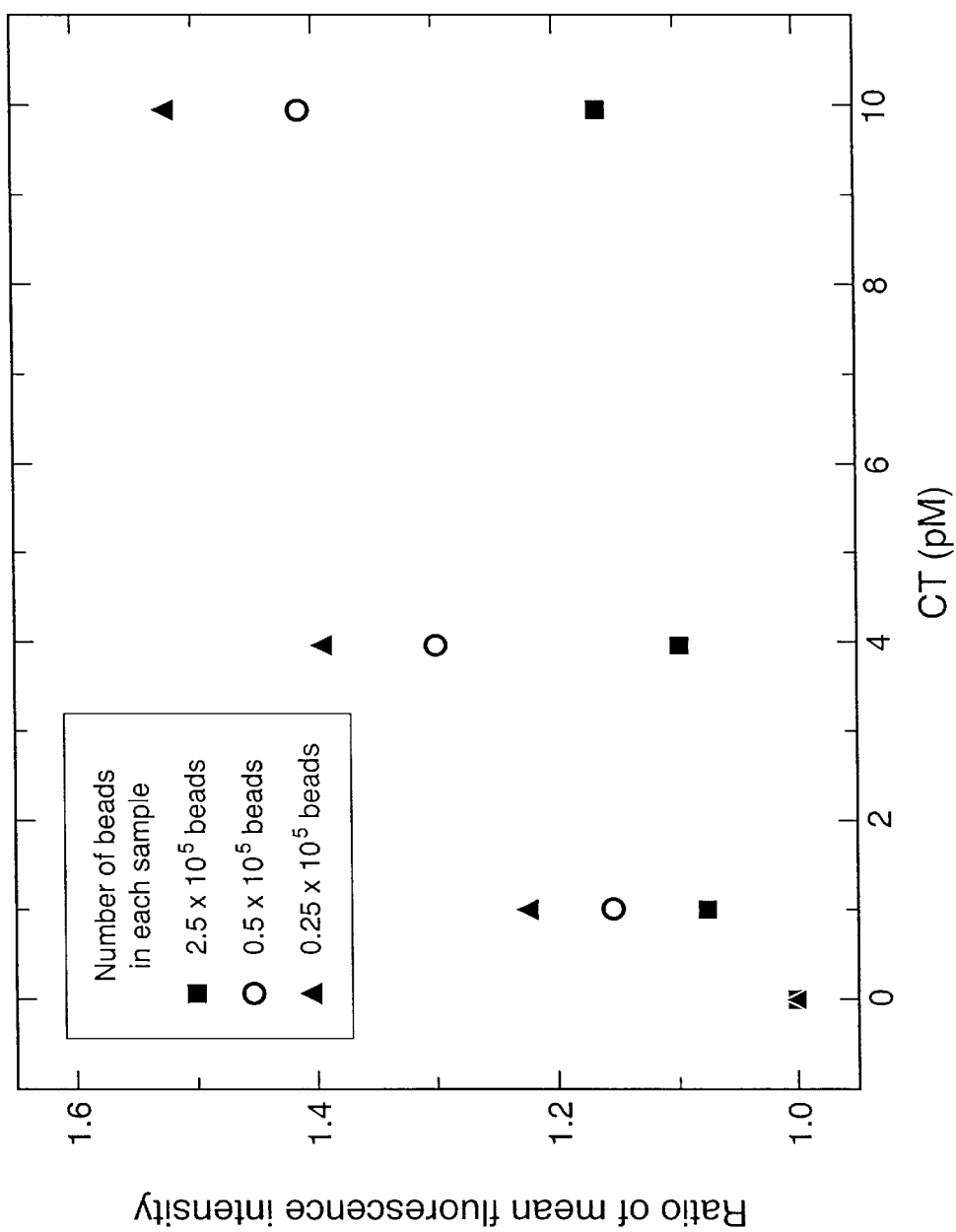
FIG. 13 shows plots of a normalized ratio of mean acceptor/donor fluorescence versus cholera toxin concentration for samples containing different number of beads coated with POPC and the labeled GM1 ([POPC]/[$B_{FL}$-GM1]/[$B_{558/568}$-GM1]=2000/1/1) where sample preparation was with an appropriate number of beads in 5 microliters of buffer incubated with 5 microliters of cholera toxin stock solution for one hour and flow cytometry measurements were taken immediately after dilution of the samples to 500 microliters such that $I_a$, $I_d$ are the mean fluorescense intensities of acceptor and donor with cholera toxin, respectively and $I_a^o$, $I_d^o$ are the mean fluorescense intensities of acceptor and donor without cholera toxin, respectively.

As anticipated by the fact that both spectrofluormeter and flow cytometer measure the fluorescence, the titration results using flow cytometry for $B_{FL}/B_{558/568}$–GM1 energy transfer system were very similar to that obtained using spectrofluorometer. The detection sensitivity and dynamic range are strongly dependent upon the total concentration of the labeled GM1 in the sample. The samples containing lower concentration of the labeled GM1 provide higher sensitivity but smaller detection dynamic range. As a result of an improvement in signal-to-noise ratio for flow cytometry, the detection sensitivity (less that 1 pM) achieved by flow cytometer is much higher than that (<100 pM) using spectrofluorometer. FIG. 13 shows the titration data only in the low range of CT concentration, where as low as 1 picomolar (pM) CT can be reliably detected. As observed by using spectrofluorometer, addition of excess CT results in saturation for the binding, and a large excess of CT actually drags down the fluorescence change. The dramatic improvement in detection sensitivity benefits from lower background, strong excitation source and sensitive fluorescence detection system built in flow cytometer. The strong laser excitation source and sensitive fluorescence detection system allow usage of only small amount of bead samples, which boosts the detection sensitivity. The high detection selectivity was demonstrated by the fact that no significant fluorescence change was observed with addition of much higher concentration of human serum albumin and peanut lectin.

Figure 14:
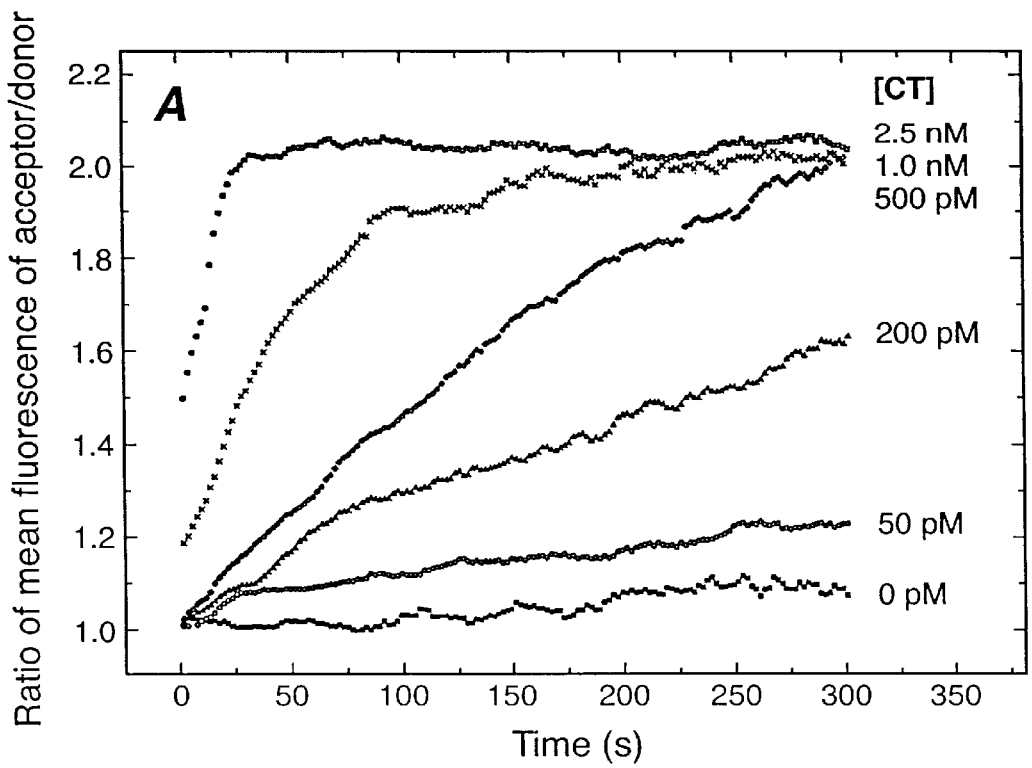
FIG. 14 shows a plot of the ratio of mean acceptor/donor fluorescence as a function of time upon addition of different amounts (concentrations) of cholera toxin measured by flow cytometry where each sample pf 500 microliters contains 2.5×105 beads coated with POPC/$B_{FL}$-GM1/$B_{558/568}$-GM1 (800/1/1) in POPC bilayers.

Detection speed is critical for sensing applications. In order to fully evaluate and optimize the performance of our sensing system in term of detection speed, we carried out a detailed study of the binding kinetics between the labeled GM1 and CT on the membrane surfaces of the glass microspheres. FIG. 14 shows the ratio of the mean fluorescence intensities of the acceptor/donor as a function of time upon addition of different concentrations of CT. Apparently, the higher the concentration of CT, the faster the binding. For example, addition of 1 nM CT requires less than 1 minute for the completion of the binding, while it takes 5 minutes for 0.5 nM CT for an identical sample. The quantitative analysis of the binding kinetics as well as dissociation kinetics of a fully complexed CT by either dilution or exchange with unlabeled natural GM1 will be reported elsewhere. Besides the concentration of CT added, the total concentration of the labeled GM1 and its surface density also play important roles. As predicted, an increase in the total number of the labeled GM1 speeds up the binding rate. When the number of beads (e.g. 104/ml) coated with the labeled GM1 and the concentration of CT in the sample (e.g. 1 pM) are extremely low, the binding process is very slow. In this case, instead of measuring the fluorescence of the sample continuously, we took the measurement intermittently to save bead samples. While not wishing to be bound by the present explanation, it is speculated that the binding kinetics is controlled by the lateral diffusion of the labeled GM1 in the membrane surfaces when the number of beads and concentration of the CT added are high, whereas the diffusion of CT in the bulk phase to the sensing surfaces of the beads is rate-determining step when both number of beads and concentration of CT are low.

In order to find out the optimal ration of $[B_{FL}-GM1]/[B_{558/568}-GM1]$ on the membrane surface to achieve maximal signal change (the ratio of acceptor/donor fluorescence) induced by CT binding, a series of samples was prepared containing ratios of $\{B_{FL}-GM1]/[B_{558/568}-GM1]$ ranging from 3:1 to 1:3 with identical surface density of the total labeled GM1. It was found (FIG. 14) that the samples with a ratio of $[B_{FL}-GM1]/[B_{558/568}-GM1]$ close to 1:1 give best results (maximal increase in the ratio of acceptor/donor fluorescence intensities). When much excess of $B_{FL}-GM1$ is used, the percentage increase of the $B_{558/568}-GM1$ fluorescence is relatively large, while the percentage increase of the $B_{FL}-GM1$ fluorescence is small. On the other hand, the increase of the $B_{558/568}-GM1$ fluorescence was small and the decrease of the $B_{FL}-GM1$ fluorescence was large when much excess of the $B_{558/568}-GM1$ is used. In both cases, the ratio increase are relatively small compared with the samples with equal moles of both $B_{FL}$- and $B_{558/568}$-labeled GM1.

Another important parameter which determines the detection performance of the sensing system is the surface density of the labeled GM1 on the bilayer membrane surfaces. On one hand, the fluorescence energy transfer can occur even without multivalent binding if the surface density is so high that the distance between the donor and acceptor is within the energy transfer range. On the other hand, the apparent binding strength (affinity) will be low (it is expected that lower the surface density, smaller the apparent affinity) if the surface density is too low. It is desired to have apparent affinity as high as possible to achieve high sensitivity. It is also expected that the bilayer surface is not perfectly homogeneous on the microspheres and the boundaries which separate continuous domains may provide some degree of barrier for individual labeled GM1 molecule to cross to accommodate multivalent binding. In the case of low surface density, each domain may not be able to provide enough number of the labeled GM1 for multivalent binding. The surface density of the labeled GM1 can also certainly influence the binding kinetics. Lower the surface density, slower the binding kinetics. In order to compromise the conflictory requirements of the surface density of the labeled GM1 for maximal fluorescence change, apparent binding affinity and kinetics, optimization of the surface density is important for the overall performance. For this reason, a series of samples with different surface densities of the labeled GM1 ($[B_{FL}-GM1]/[B_{558/568}-GM1]=1:1$) were tested in terms of maximal CT-induced fluorescence intensity, binding kinetics. It was found that samples with a surface density of the labeled GM1 of 0.4 to 0.08% show best performance in terms of CT-induced fluorescence change, apparent affinity and kinetics. When the surface density was larger than 0.2%, the background fluorescence of the acceptor was higher due to the pre-binding energy transfer. In contrast, the fluorescence change induced by CT binding was small when the surface density was too low probably owing to the limited number of the labeled GM1 available in each membrane domain and low apparent affinity.

Figure 15:
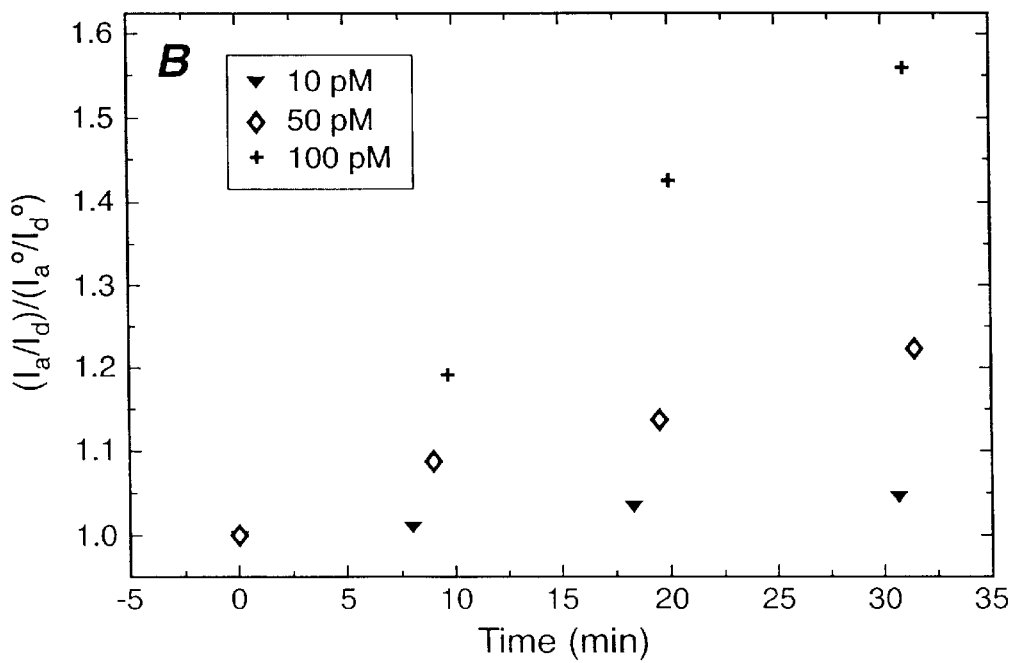
FIG. 15 shows kinetic profiles with low cholera toxin concentrations for samples identical to those described in FIG. 13.

The choice for the detection data presentation is the ratio of the mean fluorescence intensities of donor and acceptor as used above. Although the intensity ratios are convenient and reliable, it starts to level off very quickly especially for sensitive detections (small detection dynamic range) using small amount of the labeled GM1 in each sample. As shown above, besides the fluorescence intensity change, the kinetics are also closely associated with the concentration of CT present in the sample. Therefore, variation of the binding kinetics can provide another option to represent the amount of CT in the solution as well. The advantage of using kinetic data as detection parameters is the relatively larger detection dynamic range. As shown in FIG. 15, the plots of the ratio of the mean fluorescence intensities of acceptor/donor versus the time at the early state are approximately linear and the slopes can be used as an alternative for the representation of the relative binding kinetics, and as an indicator for the presence of CT. The detection dynamic range using kinetic data was larger than that using the fluorescence intensity ratio while it provided a similar level of reliability and sensitivity.

Bilayer vesicles in 50 mM tris-buffer (pH=8.0) were prepared in accordance with the process described by Hope et al., "Production of Large Unilamellar Vesicles by a Rapid Extrusion Procedure: Characterization of Size Distribution, Trapped Volume and Ability to Maintain a Membrane-Potential", Biochim. Biophys. Acta, vol. 812, pp. 55–65 (1985), such description incorporated herein by reference. A Cell Disrupter W220F from Heat Systems Ultrasonic, Inc. (setting 6.5, 35 W) was used for probe sonication. The bilayer vesicles with fluorophore-attached biotin on the outer leaflet were made according to the procedure of Felgner et al., "Asymmetric Incorporation of Trisialoganglioside into Dipalmitoylphosphatidylcholine Vesicles", Biochemistry, vol. 20, pp. 2168 (1981), by mixing the preformed bilayer vesicle of POPC with the fluorophore-attached biotin in tris-buffer overnight at room temperature.

The glass beads coated with POPC bilayers were prepared by putting the glass beads in a preformed POPC vesicle solution (0.5 to 1.3 mM) overnight at room temperature and stored at 4° C. The beads with POPC bilayers were separated from the solution by centrifugation and washed twice by tris-buffer. An aqueous solution of the labeled biotin was incubated at room temperature with the glass beads coated with POPC bilayers overnight to incorporate the labeled biotin into the outer leaf of the POPC bilayers. The number of glass beads per mg was estimated to be $1.5 \times 10^7$. The surface density of $B_{581/591}$-Biotin in the POPC bilayer coated on glass microspheres was based on assumptions that the microspheres were perfect with full coverage of POPC bilayers and the cross-section area of POPC molecules in the bilayer was 75 square angstroms ($A^2$).

0.8 mg biotin-HCl dissolved in 100 $\mu$l of 1 M sodium bicarbonate buffer (pH-8.4) was added with 1.5 mg $B_{581/}$ 591-succinimidyl ester (from Molecular Probes, Inc.) dissolved in 100 μl DMF and the mixture was then vortexed overnight. Thin layer chromatography (CH$_3$CL/methanol=100/10,R$_f$=0.4) showed appearance of a new product. The product was isolated by TLC plate and washed out by the same solvent. The solvent was removed by a nitrogen stream and was re-dissolved in methanol. Absorption spectra were taken in methanol to determine the concentration of the products based on the extinct coefficient constant of B$_{581/581}$ (ϵ=1.54×10$^5$ at 582 nm). The methanol was removed again by a nitrogen stream and an appropriate amount of tris-buffer was added. The solution was centrifuged and supernatant was transferred to a vial which was stored below 0° C.

Figure 16:
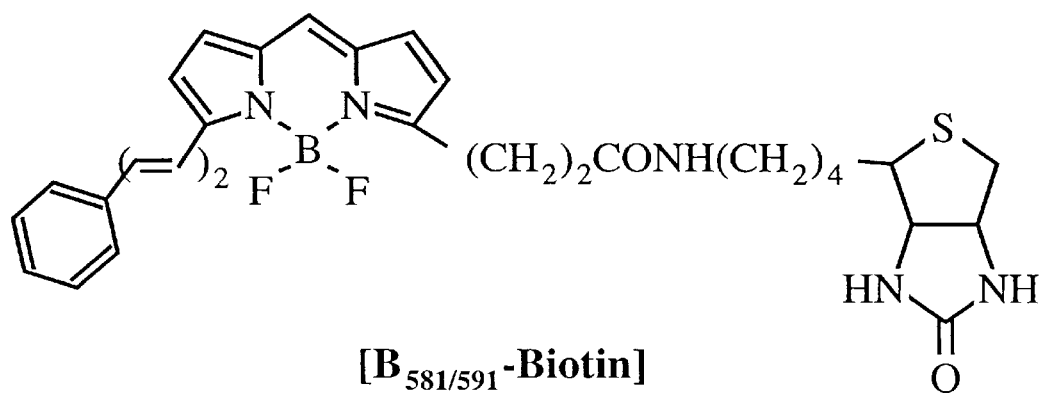
FIG. 16 shows the chemical structure of a labeled group used in the present invention.
Figure 17:
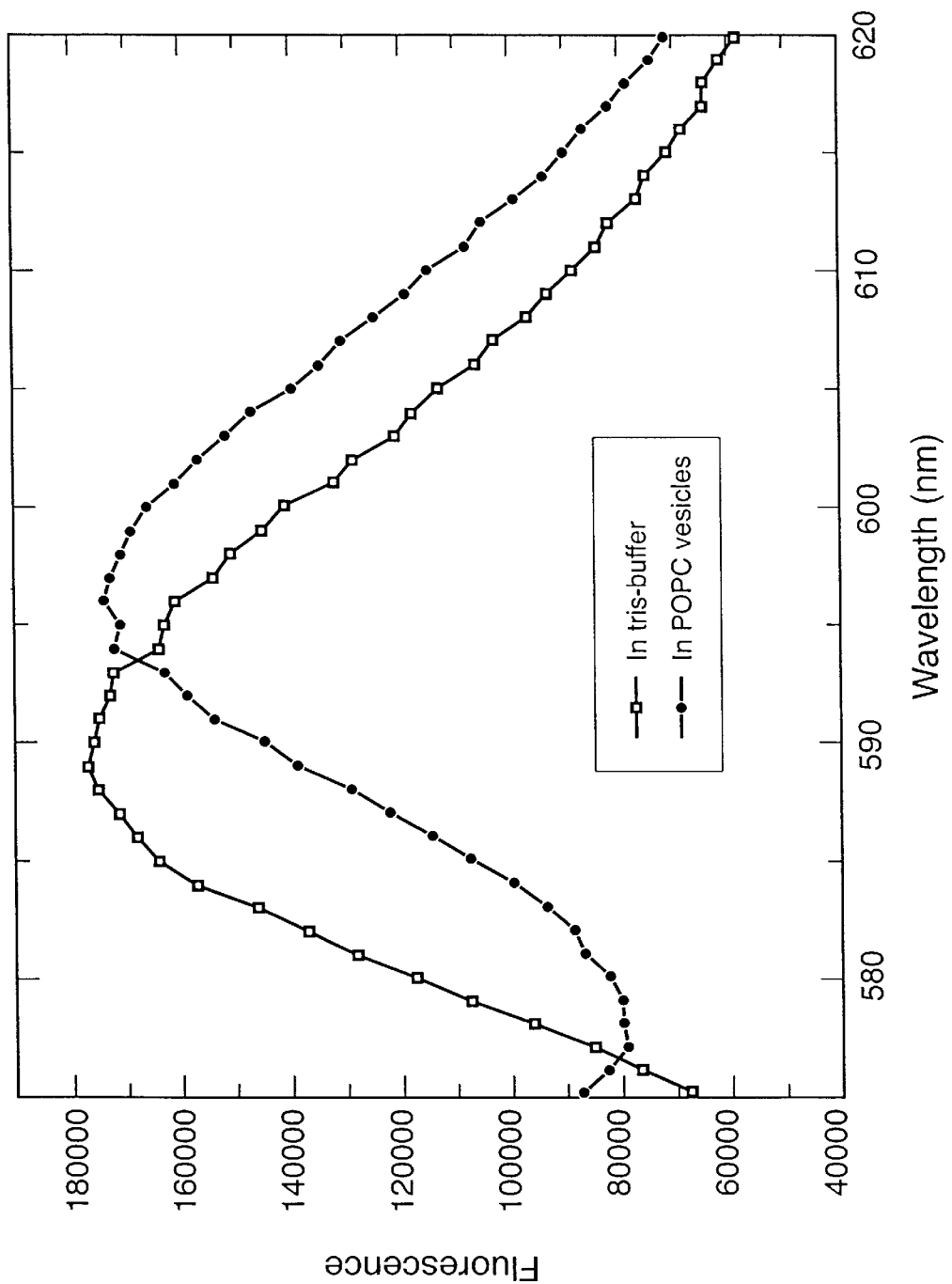
FIG. 17 shows fluorescence spectra of $B_{581/591}$-biotin (at 560 nm) in tris-buffer and POPC vesicles.

Originally, B$_{581/591}$-Biotin (see FIG. 16) was expected to have low solubility in water because of the hydrophobic BODIPY fluorophore, which allows stable incorporation of the labeled biotin in the surface of POPC bilayers. Surprisingly, it was found to be quite soluble in tris-buffer as evidenced by the findings that it shows very strong fluorescence in tris buffer and its fluorescence intensity is linearly proportional to the concentration of up to 0.45 μM. Otherwise, a weak fluorescence should be observed with aggregated fluorophores due to self-quenching. In the presence of POPC vesicles or POPC bilayers coated on glass microspheres, B$_{581/591}$-biotin prefers to anchor in the surface of POPC bilayers. As shown in FIG. 17, the fluorescence spectrum (peak at 590 mm) of B$_{581/591}$-biotin in tris buffer shifts slightly to the red region compared to that (peak at 596 nm) in the outer leaflet of POPC bilayers. The fluorescence intensity started to increase up to about 25% when POPC vesicles was added to the tris buffer solution of B$_{581/591}$-biotin. The increase in fluorescence leveled off about half-hour later, suggesting that most of B$_{581/591}$-biotin had been incorporated into the POPC bilayers. The spectral shift and intensity increase can be attributed to the environmental change from hydrophilic bulk solution to hydrophobic interior of POPC bilayers experienced by the fluorophores.

Figure 18:
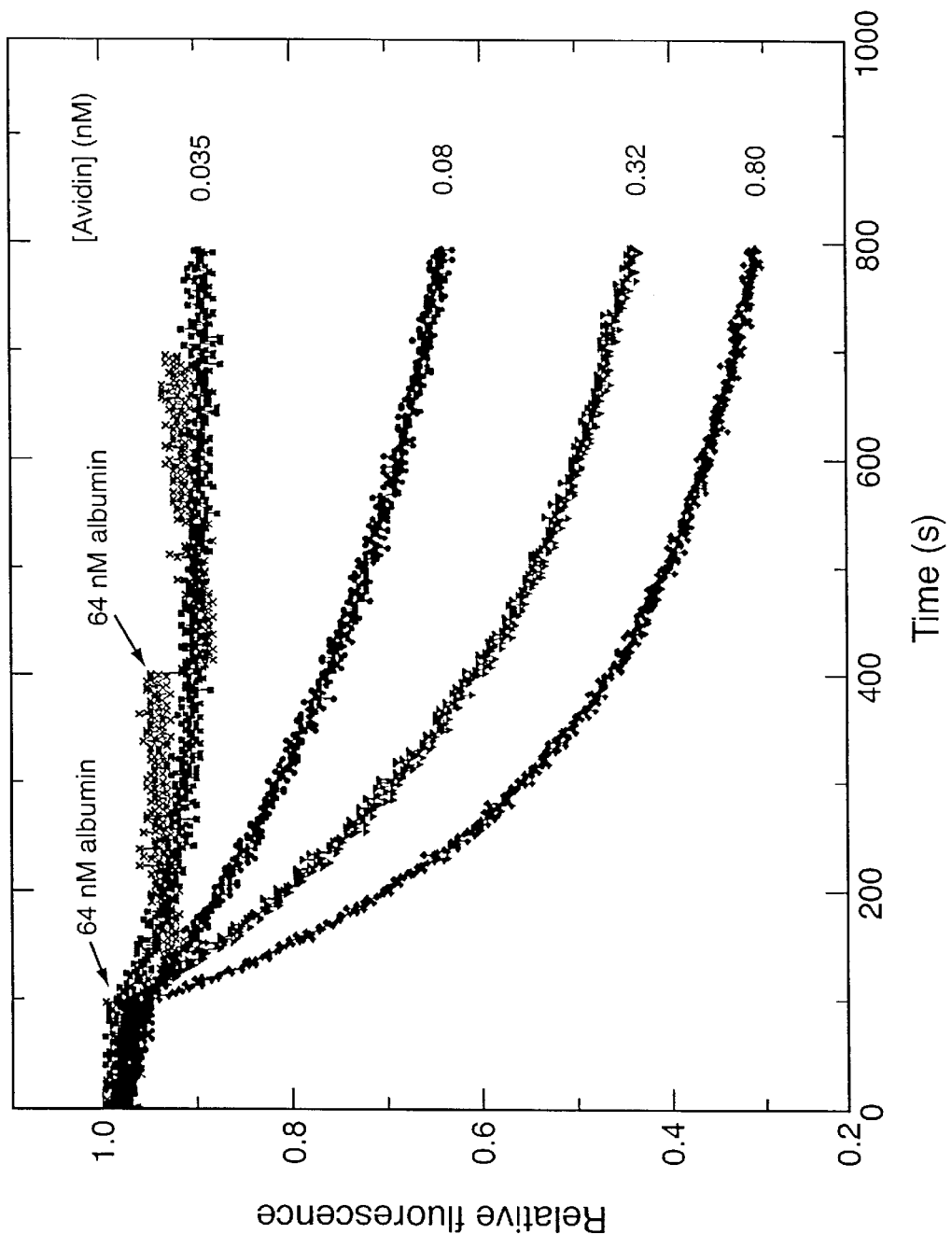
FIG. 18 shows the relative fluorescence of $B_{581/591}$-biotin (2.4 nM) in POPC bilayers coated on 0.1 mg of glass beads ([POPC]/[$B_{581/591}$-biotin] was estimated as 500) as a function of time upon addition of avidin or albumin (excited at 565 nm and monitored at 592 nm at room temperature).

Similar to observations for a fluorescein-labeled GM1/cholera toxin system in tris-buffer, the strong fluorescence of B$_{581/591}$-biotin in tris-buffer, or in the outer leaflet of POPC vesicles or POPC bilayers on glass microspheres, decreases dramatically when avidin was added. FIG. 18 shows the fluorescence intensity of B$_{581/591}$-biotin in the outer leaflet of POPC bilayers coated on glass microspheres as a function of time upon addition of avidin or albumin. Before addition of avidin, the fluorescence intensity decreases very slowly due to photobleaching. Addition of avidin causes a rapid decrease of fluorescence intensity. The degree of the decrease in fluorescence intensity reflects the amount of the avidin added. The kinetic profile also depends on the amount of the added avidin. Besides the absolute intensity change, the decrease rate of the fluorescence can also be taken as potential parameter for the concentration measurement of avidin in the solution. Higher concentration of avidin should drag down the fluorescence faster. The fluorescence change profile versus time should give valuable information about the binding kinetics. The system was tested for specificity using albumin and peanut lectin. Albumin has many hydrophobic pockets to bind the hydrphobic moieties of a molecule and peanut lectin has four binding sites for galactoside. It was found that the detection system showed high selectivity against other potential interfering proteins. For example, presence of 20 nM albumin, peanut lectin, or cholera toxin caused no measurable change in fluorescence for a sample containing 3.0 nM B$_{581/591}$-biotin, while 1 nM avidin induced more than a 75% decrease. For the same sample, 100 nM albumin or peanut lectin caused only about a 10% drop in fluorescence. The kinetic profile of the fluorescence caused by the non-specific binding of albumin and peanut lectin is also different from that induced by the specific binding of avidin. The fluorescence decreases gradually for avidin, while the presence of albumin or peanut lectin caused a sudden drop in fluorescence. This difference is also observed for CT/F-GM1 system, where cholera toxin causes the fluorescence of F-GM1 to drop gradually and albumin induces a rapid drop. The nonspecific signal is apparently caused by the nonspecific binding between albumin/peanut lectin and the fluorophore. Some evidence suggests that most of the free B$_{581/591}$-biotin prefers to stay in the bulk solution. The large, water-soluble avidin drags the labeled biotin out of the bilayer surfaces. Glass microspheres coated with POPC bilayers and B$_{581/591}$-biotin maintain most of fluorescence after washing with tris-buffer, while most of fluorescence was lost after complexing with avidin by washing.

Figure 19:
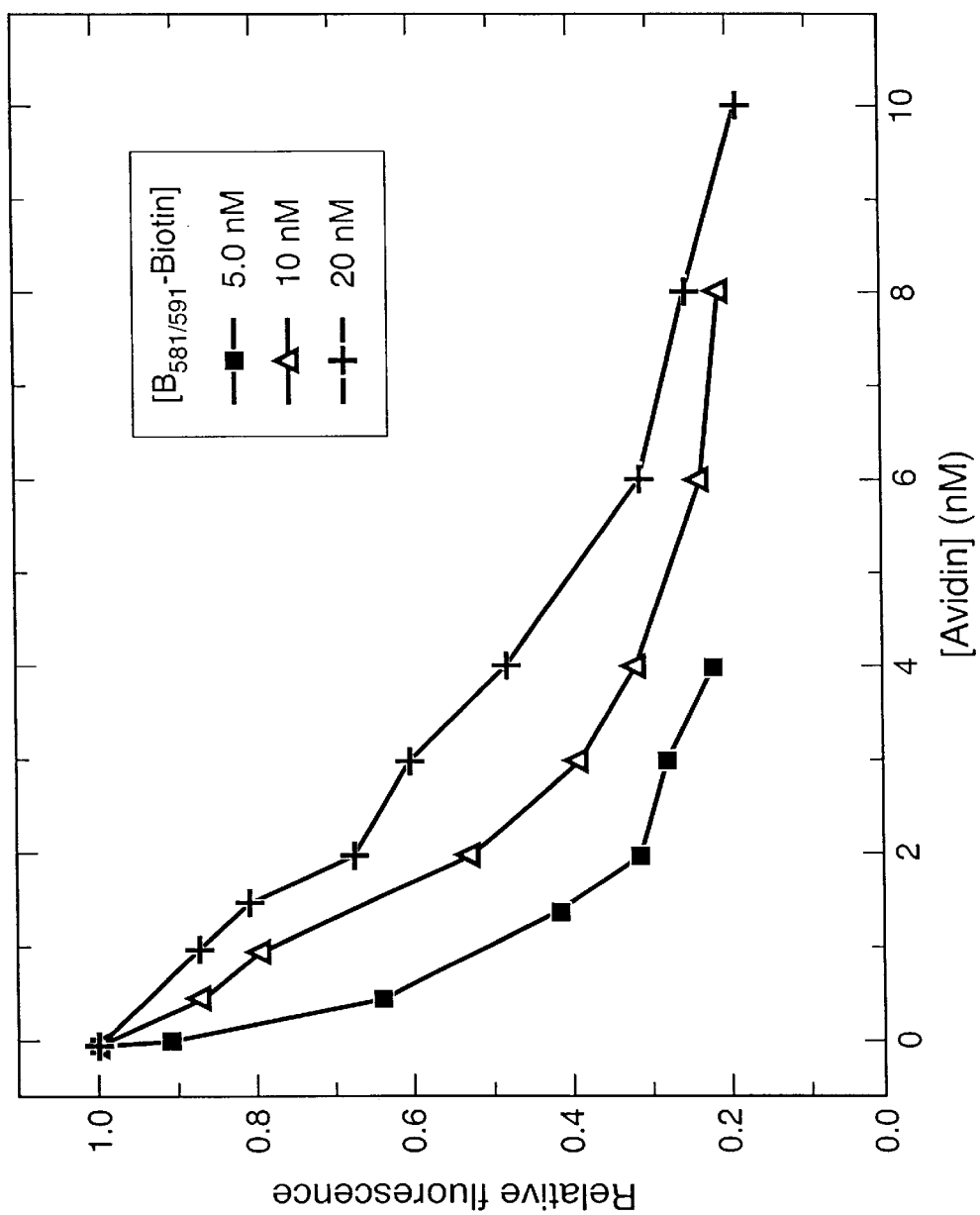
FIG. 19 shows the relative fluorescence of $B_{581/591}$-biotin in tris buffer versus avidin concentration where each set of data was obtained from a series of samples containing the same amount of $B_{581/591}$-biotin and different amounts of avidin.

The detection sensitivity and dynamic range of this method strongly depends o the total concentration of the labeled biotin. As shown in FIG. 19, the sample with low concentration of the labeled ligand provides high detection sensitivity and large detection range. It was found that either in this buffer or in the outer leaflet of POPC vesicles of POPC bilayers coated on glass microspheres, the concentration of avidin required to level off the fluorescence decrease is about one-fourth of the total concentration of the labeled biotin. This is expected for each avidin with four binding sites for biotin in tris buffer, but not o surfaces because only two binding sites on each site of avidin are available for binding on surfaces. The observation that each avidin binds with four labeled biotins in the surfaces of POPC vesicles and POPC bilayers on glass microspheres can be explained by the release of avidin/biotin complexes from the surfaces so that the binding sites on the other side become available to the labeled biotins on the surfaces.

Although the possibility that avidin can itself quench some of B$_{581/591}$-biotin fluorescence can not be excluded, there is no doubt that distance-dependent fluorescence self-quenching plays an important role in the fluorescence drop. For example, presence of 1.5 nM avidin reduces more than about 80% fluorescence for a sample containing 5 nM B$_{581/591}$-biotin, while addition of 360 nM avidin causes only about a 50% decrease in fluorescence, apparently owing to the formation of low-valent complexes, where self-quenching efficiency should be low.

Figure 20:
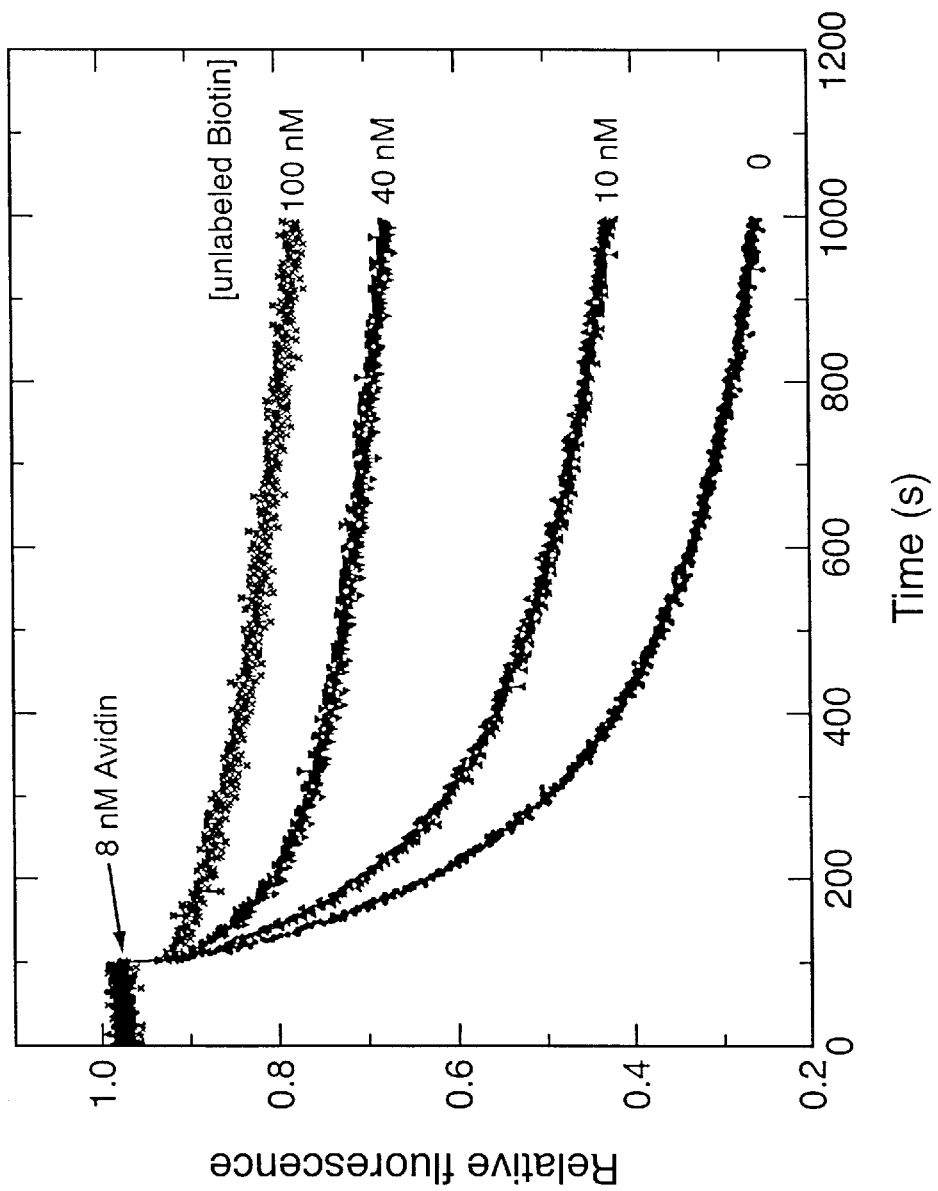
FIG. 20 shows fluorescence spectra of $B_{581/591}$-biotin (excited at 590 and monitored at 570 nm) in tris-buffer with different amounts of norbiotinamine, hydrochloride (unlabeled biotin) upon addition of 8 nM of avidin.

FIG. 20 shows the fluorescence change of B$_{581/591}$-biotin in tris buffer with different concentrations of unlabeled biotin for competitive binding upon addition of avidin. Without the presence of the unlabeled biotin, the fluorescence decreases more than 75 percent and most of the labeled biotins are expected to bins with the avidin. When more unlabeled biotins are added, the fluoresecence decrease was inhibited due to the competitive binding of the unlabeled biotins so that less labeled biotins bind with the avidin. Similar to the direct detection of avidin, the sensitivity and dynamic range of biotin detection was also strongly dependent on the concentration of the labeled biotin and avidin. A sample with low concentration of labeled biotin and avidin yielded high sensitivity and a small dynamic range while a sample containing high concentrations of labeled biotin and avidin yielded low sensitivity but a large dynamic range. This competitive assay method could reliably detect less than 0.2 nM of biotin. Due to the high affinity between biotin/avidin interaction, the replacement of the labeled biotin already bound to avidin is extremely slow and takes more than four days by the unlabeled biotin. So, one procedure for the competitive assay would be by addition of a proper amount of avidin to a sample containing a known amount of the labeled biotin and an unknown amount of the free biotin, not by sequential addition.

Such a procedure for competitive assay can be used with other materials substituted for the biotin and avidin. Such a competitive assay procedure can be important in analysis for selected target biomolecules or ligands.

Figure 21:
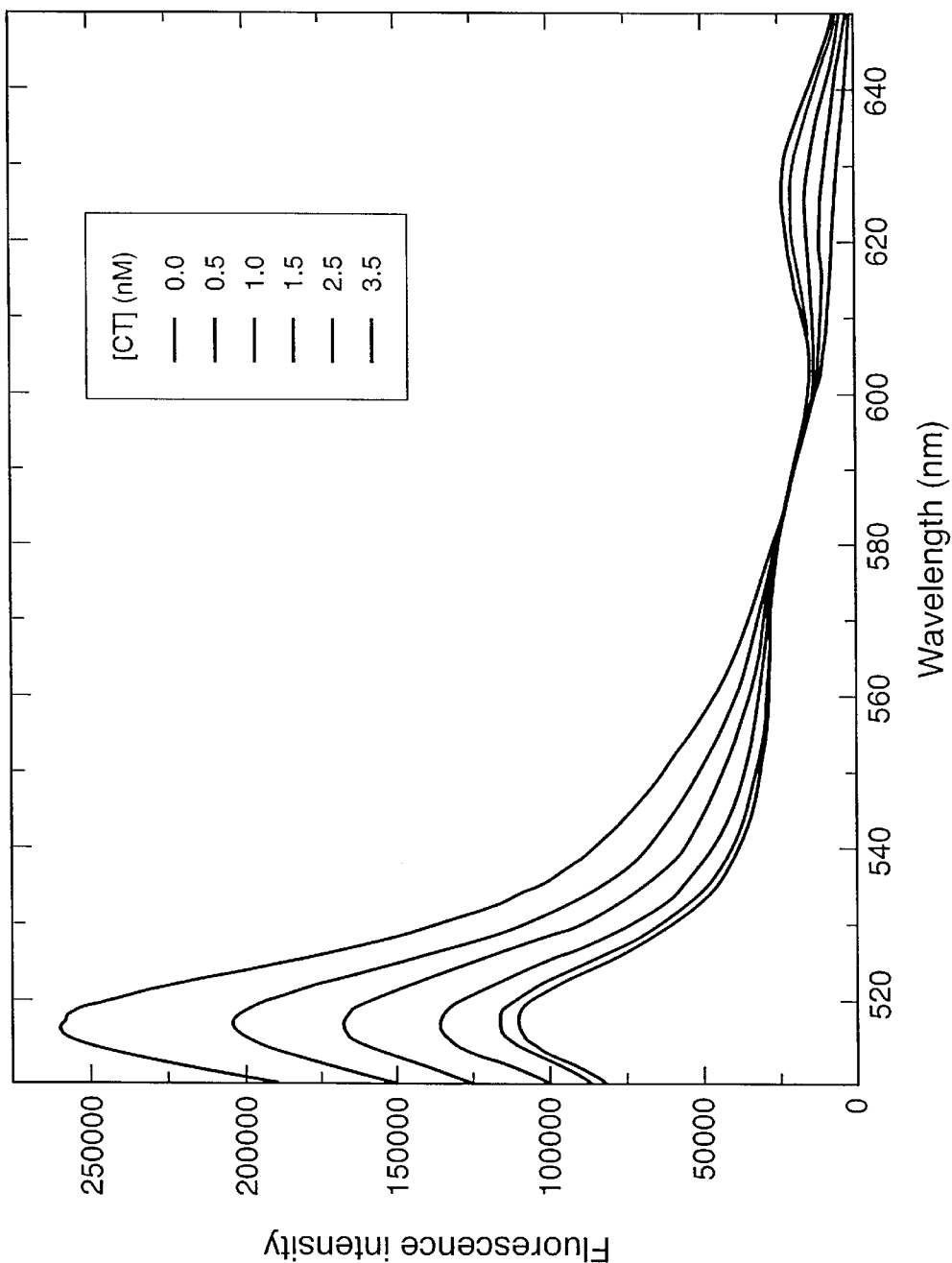
FIG. 21 shows the fluorescence spectra of the three labeled GM1 molecules in POPC liposomes in the presence of different concentrations of cholera toxin.
Figure 22:
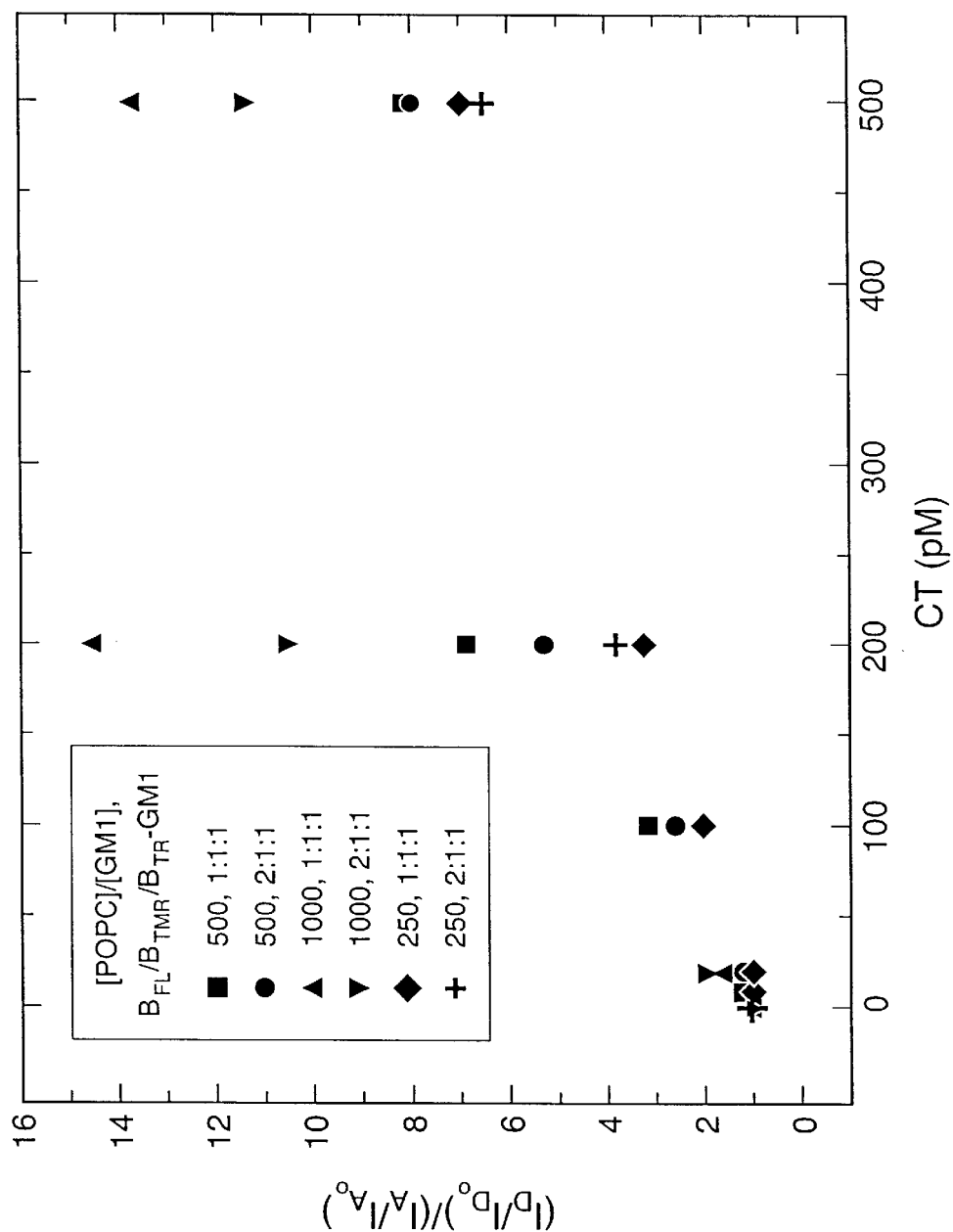
FIG. 22 shows the titration data of the three labeled GM1 molecules in POPC bilayers coated on glass bead measured by flow cytometry.

In another embodiment, the distance-dependent fluorescence energy transfer process induced by multivalent interactions in the present invention can be extended to two-stage energy transfer-based signal transduction for detection of species involved in multivalent interactions. The advantage of the two-stage energy transfer process over a one stage energy transfer process is the low fluorescence background of the acceptor prior to the binding achieved by the fact that little acceptor is excited due to the large absorption wavelength separation between the donor and acceptor achieved by the intermediate fluorphore. The requirement for efficient two-tiered energy transfer is the significant overlap between the emission of the intermediate and excitation of the acceptor. BFL (donor), BTMR (intermediate) and BTR can meet this requirement. The three fluorophore-tagged GM1 molecules were incorporated into the outer leaflet (layer) of the POPC bilayers either in the form of liposomes or coated on glass bead surfaces. The aggregation of the three labeled GM1 molecules induced by cholera toxin binding triggered a two-stage energy transfer, resulting in an increase in acceptor fluorescence and a decrease in donor fluorescence. FIG. 21 shows the fluorescence spectra of the three labeled GM1 molecules in POPC liposomes in the presence of different concentrations of cholera toxin. FIG. 22 shows the titration data of the three labeled GM1 molecules in POPC bilayers coated on glass bead measured by flow cytometry.

The present biosensor invention is considered to be general in nature. Thus, it can be applicable to the detection of any multivalent biomolecule, e.g., multivalent proteins, antibodies, enzymes and the like. Thus, any biomolecule that has multiple epitopes and can be recognized by the same recognition unit (either antibody or receptor) or multiple recognition units that recognize different epitopes of the same protein can be detected. The use of multiple dye molecules with distinct excitation and emission spectra that are used to tag either one or more recognition units is one key to the sensor of the present invention. The present invention may also be used in the detection of biomolecules such as viruses where, e.g., some signature protein of the virus may be detected in the same manner as other biomolecules.

Among the primary parts of the present invention presented here are:

functionalization of naturally occuring glycolipid receptors (e.g., GM1) with an optical tag such as fluorescent dye molecules;

fabrication of biomimetic membranes (supported and hybrid phospholipid bilayers) containing the functionalized (optically tagged) glycolipid receptor;

use of donor and acceptor dye molecules each of which is covalently attached to the GM1 to effect energy transfer upon aggregation following binding by a multivalent protein;

use of hydrophobic optical tags (dye molecules) and a hydrophobic linker molecules to attach the dye to the glycolipid so that the dye molecule resides in the upper leaf of the phospholipid bilayer thereby minimizing non-specific interactions of the dye molecule with interferents;

optical transduction that is triggered by a specific protein binding event which results in an energy transfer scheme yielding both a decrease in the fluorescence of one dye species (e.g., blue emission) with a concomitant increase in the fluorescence of another dye species (e.g., red emission);

optical signal transduction resulting from an internal reference by virtue of the simultaneous increase in a red fluorescence and a decrease in a blue fluorescence coupled with an isobestic point that can be used to reference the absolute intensity of fluorescence;

signal transduction based on aggregation of receptor molecules through either binding by a multivalent protein or binding of multiple receptors to the same protein;

an optical transduction approach that amplifies specific binding events thereby amplifying both sensitivity and specificity; and, use of optically tagged receptor molecules to trigger signal transduction and amplification by a recognition event.

The sensor of the present invention relies upon fluidity in the artificial membrane bilayer. Since most artificial membranes (i.e., supported bilayers and hybrid bilayers) are inherently unstable, the issue must be dealt with. Stable bilayers with fluid upper leafs (layers) using a variety of approaches have previously been created, some of which mimic therophillic bacterial and their stable membranes.

As used herein the term "receptor" is used in its broadest context. Receptor can refer to any chemical entity capable of binding to the desired target molecule. Thus, the receptor is any compound or composition capable of recognizing another target species or molecule. Natural receptors include antibodies, enzymes, lectins, and the like. For example, the receptor for an antigen is an antibody while the receptor for an antibody is either an anti-antibody or preferably, the antigen recognized by that particular antibody.

As used herein the term "recognition molecule" refers to a molecule that binds in a multivalent fashion, preferably selectively, to a target biomolecule.

As used herein the term "recognition event" refers to the event whereupon a recognition molecule binds in a multivalent fashion, preferably selectively, to a target biomolecule.

As used herein the term "transduction" refers to the act registering the presence of a chemical entity such as a biomolecule through attachment or binding of a recognition molecule to the biomolecule with some transfer of information such as a measurable change resulting due to the attachment or binding to the biomolecule.

Further description of the present invention is found in Song et al., "Optical Signal Transduction Triggered by Protein-Ligand Binding: Detection of Toxins Using Multivalent Receptors", Journal of the American Chemical Society, vol. 120, no. 4, pp. 4873–4874, May 20, 1998, in Song et al., "An Optical Biosensor Based on Fluorescence Self-Quenching and Energy Transfer: Ultrasensitive and Specific Detection of Protein Toxins", Journal of the American Chemical Society, vol. 120, no. 44, pp. 11514–11515, Nov. 11, 1998, and Song et al., "Direct, Ultrasensitive, and Selective Optical Detection of Protein Toxins Using Multivalent Interactions", Analytical Chemistry, vol. 71, pp. 2097–2107, 1999, such descriptions incorporated herein by reference.

Although the present invention has been described with reference to specific details, it is not intended that such details should be regarded as limitations upon the scope of the invention, except as and to the extent that they are included in the accompanying claims.

What is claimed is:

1. An optical biosensor for detection of a multivalent target biomolecule comprising:

a substrate having a fluid membrane thereon;

recognition molecules situated at a surface of said fluid membrane, said recognition molecule capable of binding with said multivalent target biomolecule and said recognition molecule linked to a single fluorescence molecule and as being movable upon said surface of said fluid membrane; and, a means for measuring a change in fluorescent properties in response to binding between multiple recognition molecules and said multivalent target biomolecule.

2. A method of detecting a multivalent target biomolecule comprising:

contacting a sample with a sensor including a substrate having a fluid membrane thereon, recognition molecules situated at a surface of said fluid membrane, said recognition molecule capable of binding with said multivalent target biomolecule and said recognition molecule linked to a single fluorescence molecule and as being movable upon said surface of said fluid membrane; and measuring a change in fluorescent properties in response to binding between multiple recognition molecules and said multivalent target biomolecule.

3. An optical biosensor for detection of a multivalent target biomolecule comprising:

a substrate having a fluid membrane thereon;

at least two different recognition molecules situated movably upon a surface of said fluid membrane, said recognition molecules capable of binding with said multivalent target biomolecule wherein at least one of said recognition molecules is linked to a single fluorescence donor molecule and at least another of said recognition molecules is linked to a single fluorescence acceptor molecule; and, a means for measuring a change in fluorescent properties in response to binding between said two different recognition molecules and said multivalent target biomolecule.

4. The optical biosensor of claim 3 wherein the recognition molecule is contained within an upper layer of a bilayer surface.

5. A method of detecting a multivalent target biomolecule comprising:

contacting a sample with a sensor including a substrate having a fluid membrane thereon and at least two different recognition molecules situated movably upon a surface of said fluid membrane, said recognition molecules capable of multivalent binding with said multivalent target biomolecule wherein at least one of said recognition molecules is linked to a single fluorescence donor molecule and at least another of said recognition molecules is linked to a single fluorescence acceptor molecule; and measuring a change in fluorescence in response to binding between said two different recognition molecules and said multivalent target biomolecule.

6. An optical biosensor for detection of a multivalent target biomolecule comprising:

a recognition molecule capable of binding with said multivalent target biomolecule wherein said recognition molecule is linked to a single fluorescence molecule selected from the group consisting of a fluorescence donor molecule and a fluorescence acceptor molecule thereon;

a supporting surface for said recognition molecule, wherein said supporting surface includes a fluorescence label selected from the group consisting of a fluorescence donor label and a fluorescence acceptor label thereon wherein said supporting surface including the fluorescence donor label when said recognition molecule includes the single fluorescence acceptor molecule and said supporting surface including the fluorescence acceptor label when said recognition molecule includes the single fluorescence donor molecule; and, a means for measuring a change in fluorescent properties in response to binding between multiple recognition molecules and said multivalent target biomolecule.

7. The optical biosensor of claim 6 wherein said recognition molecule is labeled with a single fluorescence donor molecule and said supporting surface is a phospholipid bilayer labeled with a fluorescence acceptor label.

8. The optical biosensor of claim 7 wherein said multivalent target biomolecule is cholera, said recognition molecule is ganglioside GM1 labeled with a singe fluorescence donor molecule selected from the group consisting of DABCY and BODIPY-FL and said phospholipid bilayer supporting surface is beta-palmitoyl-gamma-oleoyl-L-alpha-phosphatidylcholine labeled with a fluorescence acceptor label of pyrene.

9. The optical biosensor of claim 6 wherein the supporting surface is a phospholipid bilayer and the recognition molecule is contained within an upper layer of the bilayer surface.

10. The optical biosensor of claim 6 wherein the fluorescence label upon the recognition molecule has the fluorescent properties of self-quenching.

11. An optical biosensor for the detection of a target biomolecule comprising:

a substrate having a fluid membrane thereon;

recognition molecules situated at a surface of said fluid membrane, said recognition molecule bound with a selected multivalent biomolecule, said recognition molecules, each linked to a single fluorescence molecule; and, a means for measuring a change in fluorescent properties in response to competitive binding with said selected multivalent biomolecule by said recognition molecules and said target biomolecule.

* * * * *